US008597907B2

(12) United States Patent
Date et al.

(10) Patent No.: US 8,597,907 B2
(45) Date of Patent: Dec. 3, 2013

(54) METHOD OF PRODUCING PROTEINS

(75) Inventors: Masayo Date, Kawasaki (JP); Yoshimi Kikuchi, Kawasaki (JP); Hiroshi Itaya, Kawasaki (JP); Nami Nakamura, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1203 days.

(21) Appl. No.: 11/550,972

(22) Filed: Oct. 19, 2006

(65) Prior Publication Data

US 2007/0184525 A1 Aug. 9, 2007

Related U.S. Application Data

(63) Continuation of application No. PCT/JP2005/007518, filed on Apr. 20, 2005.

(30) Foreign Application Priority Data

Apr. 20, 2004 (JP) ................................ 2004-124196
Jan. 13, 2005 (JP) ................................ 2005-005896

(51) Int. Cl.
*C12P 21/06* (2006.01)
*C12N 9/10* (2006.01)
*C12N 1/21* (2006.01)
*C12N 15/00* (2006.01)
*C07H 21/04* (2006.01)

(52) U.S. Cl.
USPC ..................... 435/69.1; 435/193; 435/252.33; 435/320.1; 536/23.2

(58) Field of Classification Search
None
See application file for complete search history.

(56) References Cited

U.S. PATENT DOCUMENTS

| 4,965,197 | A | 10/1990 | Liebl et al. |
| 6,022,952 | A | 2/2000 | Weiner et al. |
| 6,027,920 | A | 2/2000 | Joliff et al. |
| 6,335,178 | B1 | 1/2002 | Weiner et al. |
| 2002/0110860 | A1* | 8/2002 | Bron et al. .................... 435/69.1 |
| 2003/0082746 | A1 | 5/2003 | Kikuchi et al. |
| 2004/0126847 | A1 | 7/2004 | Kikuchi et al. |
| 2006/0019367 | A1 | 1/2006 | Umezawa et al. |

FOREIGN PATENT DOCUMENTS

| EP | 1219713 | 7/2002 |
| JP | 6-502548 | 3/1994 |
| JP | 6-169780 | 6/1994 |
| JP | 6-277073 | 10/1994 |
| JP | 7-107981 | 4/1995 |
| JP | 11-169182 | 6/1999 |
| WO | WO01/23591 | 4/2001 |
| WO | WO02/22667 | 3/2002 |
| WO | WO02/081694 | 10/2002 |
| WO | WO 03/083056 A2 * | 10/2003 |
| WO | WO2004/011492 | 2/2004 |
| WO | WO2005/103278 | 11/2005 |

OTHER PUBLICATIONS

UniProt Accession No. Q6M593, TatC (created on Jul. 5, 2004).*
Blaudeck, N., et al., "Specificity of Signal Peptide Recognition in Tat-Dependent Bacterial Protein Translocation," J. Bacteriol. 2001;183(2):604-610.
Date, M., et al., "Production of Native-Type *Streptoverticillium mobaraense* Transglutaminase in *Corynebacterium glutamicum*," Appl. Environmen. Microbiol. 2003;69(5):3011-3014.
Jongbloed, J. D. H., et al., "Selective Contribution of the Twin-Arginine Translocation Pathway to Protein Secretion in *Bacillus subtilis*," J. Biol. Chem. 2002;277(46):44068-44078.
Pop, O., et al., "The Twin-arginine Signal Peptide of PhoD and the TatA$_d$/C$_d$ Proteins of *Bacillus subtilis* Form an Autonomous Tat Translocation System," J. Biol. Chem. 2002;277(5):3268-3273.
Pop, O., et al., "Sequence-specific Binding of pre PhoD to Soluble TatA$_d$ Indicates Protein-mediated Targeting of the Tat Export in *Bacillus subtilis*," J. Biol. Chem. 2003;278(40):38428-38436.
Stanley, N. R., et al., "The Twin Arginine Consensus Motif of Tat Signal Peptides Is Involved in Sex-independent Protein Targeting in *Escherichia coli*," J. Biol. Chem. 2000;275(16):11591-11596.
Barrett, C. M. L., et al., "Quantitive export of a reporter protein, GFP, by the twin-arginine translocation pathway in *Escherichia coli*," Biochem. Biophys. Res. Comm. 2003;304:279-284.
Billman-Jacobe, H., et al., "Expression and Secretion of Heterologous Proteases by *Corynebacterium glutamicum*," Appl. Environmen. Microbiol. 1995;61(4):1610-1613.
Chaddock, A. M., et al., "A new type of signal peptide: central role of a twin-arginine motif in transfer signals for the ΔpH-dependent Thylakoidal protein translocase," The EMBO Journal 1995;14(12):2715-2722.
Corvey, C., et al., "Activation of subtilin precursors by *Bacillus subtilis* extracellular serine proteases subtilisin (AprE), WprA, and Vpr," Biochem. Biophys. Res. Comm. 2003;304:48-54.
Hynds, P. J., et al., "The Sec-independent Twin-arginine Translocation System Can Transport Both Tightly Folded and Malfolded Proteins Across the Thylakoid Membrane," J. Biol. Chem. 1998;273(52):34868-34874.
Iwai, A., et al., "Molecular Cloning and Expression of an Isomalto-Dextranase Gene from *Arthrobacter globiformis* T6," J. Bacteriol. 1994;176(24):7730-7734.
Jongbloed, J. D. H., et al., "TatC Is a Specificity Determinant for Protein Secretion via the Twin-arginine Translocation Pathway," J. Biol. Chem. 2000;275(52):41350-41357.

(Continued)

*Primary Examiner* — Robert Mondesi
*Assistant Examiner* — Iqbal H Chowdhury
(74) *Attorney, Agent, or Firm* — Shelly Guest Cermak; Cermak Nakajima LLP

(57) ABSTRACT

The present invention provides a method for efficiently producing an industrially useful protein in coryneform bacteria, and more particularly, a method for efficiently producing a protein for which secretion was difficult using conventional protein secretion pathways. In particular, the present invention provides a method for efficiently producing heterologous proteins comprising culturing coryneform bacteria containing an genetic construction containing a promoter sequence which functions in coryneform bacteria, a nucleic acid sequence encoding a Tat system-dependent signal peptide region, and a nucleic acid sequence encoding a heterologous protein, in the direction from 5'-end to 3'-end, and secretory producing the heterologous protein by coryneform bacteria.

12 Claims, No Drawings

(56) References Cited

OTHER PUBLICATIONS

Kikuchi, Y., et al., "Secretion of Active-Form *Streptoverticillium mobaraense* Transglutaminase by *Corynebacterium glutamicum*: Processing of the Pro-Transglutaminase by a Cosecreted Subtilisin-Like Protease from *Streptomyces albogriseolus*," Appl. Environmen. Microbiol. 2003;69(1);358-366.

Liebl, W., et al., "Expression, Secretion, and Processing of Staphylococcal Nuclease by *Corynebacterium glutamicum*," J. Bacteriol. 1992;174(6):1854-1861.

Salim, K., et al., "Heterologous Expression of the *Mycobacterium tuberculosis* Gene Encoding Antigen 85A in *Corynebacterium glutamicum*," Appl. Environmen. Microbiol. 1997;63(11):4392-4400.

Sargent, F., et al., "Overlapping functions of components of a bacterial Sec-independent protein export pathway," The EMBO Journal 1998;17(13):3640-3650.

Settles, A. M., et al., "Sec-Independent Protein Translocation by the Maize Hcf106 Protein," Science 1997;278:1467-1470.

Yamaguchi, S., et al., "Protein-glutaminase from *Chryseobacterium proteolyticum*, an enzyme that deamidates glutaminyl resudeies in proteins, Prufication, characterization and gene cloning," Eur. J. Biochem. 2001;268:1410-1421.

International Search Report for PCT App. No. PCT/JP2005/007518 (May 31, 2005).

Written Opinion of the International Searching Authority for PCT App. No. PCT/JP2005/007518 (May 31, 2005).

Bolhuis, A., et al., "TatB and TatC Form a Functional and Structural Unit of the Twin-arginine Translocase from *Escherichia coli*," J. Biol. Chem. 2001;276(23):20213-20219.

Brüser, T., "The twin-arginine translocation system and its capability for protein secretion in biotechnological protein production," Appl. Microbiol. Biotechnol. 2007;76:35-45.

De Keersmaeker, S., et al., "Evaluation of TatABC overproduction on Tat- and Sec-dependent protein secretion in *Streptomyces lividans*," Arch. Microbiol. 2006;186:507-512.

Papish, A. L., et al., "The Twin-arginine Leader-binding Protein, DmsD, Interacts with the TatB and TatC Subunits of the *Escherichia coli* Twin-arginine Translocase," J. Bio. Chem. 2003;278(35):32501-32506.

Schaerlaekens, K., et al., "Comparison of the Sec and Tat secretion pathways for heterologous protein production by *Streptomyces lividans*," J. Biotechnol. 2004;112:279-288.

Settles, A. M., et al., "Old and new pathways of protein export in chloroplasts and bacteria," Trends Cell Biol. 1998;8:494-501.

Ikeda, M., et al., "The *Corynebacterium glutamicum* genome: features and impacts on biotechnological processes," Appl. Microbiol. Biotechnol. 2003;62:99-109.

Kikuchi, Y., et al., "Functional Analysis of the Twin-Arginine Translocation Pathway in *Corynebacterium glutamicum* ATCC 13968," Appl. Environmen. Microbiol. 2006;72(11):7183-7192.

Palmer, T., et al., "Export of complex cofactor-containing proteins by the bacterial Tat pathway," Trends in Microbiology 2005;13(4):175-180.

Supplementary European Search Report for EP Patent App. No. 05734619.9 (Aug. 29, 2011).

\* cited by examiner

SEQUENCE LISTING

```
<160> NUMBER OF SEQ ID NOS: 67

<210> SEQ ID NO 1
<211> LENGTH: 1911
<212> TYPE: DNA
<213> ORGANISM: Arthrobacter globiformis
<220> FEATURE:
<221> NAME/KEY: misc_feature
<223> OTHER INFORMATION: IMD Enzyme; nucleotide sequence

<400> SEQUENCE: 1
atgatgaacc tgtcccgccg cacattgctc accaccggca gcgccgccac cctcgcctac      60
gccttgggca tggcaggctc cgcccaggcc gccaccgccg tcaccgcccg cccgggcgtc     120
cccgtcacgg ccgcgccgcc cttgcgcctg gccagccgga acagcgtgtt cacccgcagc     180
ggtgccggcc cccggtactg gaacatctac ggctactcgt tcccgcacaa cgcccccatt     240
ccggaaaacg agtggaaggc caacatcgac tggctggccg gaaacttcgc cgatttcggt     300
tacgacatcg cctgcaccga cggctggatc gaaggctcca gccgcaccac cggcaacggc     360
tacatcacca gctacaacga ttcctggcag cacgactggg cttactgggc aaactacctg     420
gccgcgcgga agatgaagct gggtgtctac tacaaccccc tctgggtgca ccgggccgcc     480
gtcgaagacg cttccaagac cgtcctgggc cggcccgacg tcaagatcgc ggacctggtg     540
gtgcccgggg acttcttcgc ccgggacatc ggcggaaacc agctgtactg gctggacgtg     600
accaagtccg gcgccaagga atacgtccag ggctacgtgc gctacttcaa ggacctcggc     660
gttccctacc tgcggatcga cttcctctcc tggtacgagg acggaaggga cgcgaacatc     720
gggcaggtca acgcaccgca cggccgggcc aactacgaac tcgccctctc ctggatcaac     780
gaggccgccg gcgaggacat ggaagtttcg ctcgtaatgc cgcacatgtt ccaggacggt     840
tccgcggaac tggccaacgg cgacctggtg cggatcaatg ccgacgccga caagggcggc     900
tgggaccggc tgagcgggat gcgccagaac tggcaggacg cgtggcccaa ctgggccaac     960
ccgttctgcg ggttcaccgg atggtcccac cgcaacggca ggggccagct gatcctggac    1020
ggcgacttca tgcgcgccag cacctttgcc agcgacgagg aacgcaagac catgatgaac    1080
ctgatggtcg cggccggatc accccttggc atcgctgaca cctaccagca aatcggcaac    1140
aacgcctggg tttacaccaa caaggaagtc ctccagctca atgccgacgg cctggtgggc    1200
aagcccctct accggtccgc caccccgttc tccaaggacc ccggctcccg cgacaccgaa    1260
cgctgggccg gcagcttcc ggacggttcg tggggcgttg cgctcttcaa ccgcagcgac    1320
actgaaacgg tcaccaagac catcgacttc gcaaaggacc tcggcctggc aaccggcggc    1380
aacgtccggg acctctggga gcacaggaac ctgggcatgg actcccgcgc cacggccgcg    1440 ctggcccgc acgcctcggc catcttccgc gtcactccgc cgaagatgca cggcaccacc    1500
cggtaccccg cggccttcgc agcctgggga ggcggggccg gcttcaacaa caaccacccc    1560
```

-continued

```
gggtatgacg gcaacggctt cgtggacgga ctccaggcgg gctccggcag cgcggacccg    1620
ctggtcacgt tcgcggtcca ggtgccgcac cgcggcagct acgccatccg ctaccggtat    1680
gccaatgcca ccggcgatac cagcaccatg acggtcaccg ccgaaaaggc ggaccgttcc    1740
accgtggacg gtccggtcca cgtcagcttc ccgggcctgg ccacctggga cacctggggc    1800
gtggcggacg gcaccatcac gctcgatgcc ggcctgaacc tggtcaccat cggcagggc    1860 gccacggaca agggagccat caacctgaac tggatagagt tggacatgtg a            1911
```

<210> SEQ ID NO 2
<211> LENGTH: 636
<212> TYPE: PRT
<213> ORGANISM: Arthrobacter globiformis
<220> FEATURE:
<221> NAME/KEY: MISC_FEATURE
<223> OTHER INFORMATION: IMD Enzyme; amino acid sequence

<400> SEQUENCE: 2

```
Met Met Asn Leu Ser Arg Arg Thr Leu Leu Thr Thr Gly Ser Ala Ala
1               5                   10                  15

Thr Leu Ala Tyr Ala Leu Gly Met Ala Gly Ser Ala Gln Ala Ala Thr
                20                  25                  30

Ala Val Thr Ala Arg Pro Gly Val Pro Val Thr Ala Ala Pro Pro Leu
            35                  40                  45

Arg Leu Ala Ser Arg Asn Ser Val Phe Thr Arg Ser Gly Ala Gly Pro
        50                  55                  60

Arg Tyr Trp Asn Ile Tyr Gly Tyr Ser Phe Pro His Asn Ala Pro Ile
65                  70                  75                  80

Pro Glu Asn Glu Trp Lys Ala Asn Ile Asp Trp Leu Ala Gly Asn Phe
                85                  90                  95

Ala Asp Phe Gly Tyr Asp Ile Ala Cys Thr Asp Gly Trp Ile Glu Gly
            100                 105                 110

Ser Ser Arg Thr Thr Gly Asn Gly Tyr Ile Thr Ser Tyr Asn Asp Ser
        115                 120                 125

Trp Gln His Asp Trp Ala Tyr Trp Ala Asn Tyr Leu Ala Ala Arg Lys
    130                 135                 140

Met Lys Leu Gly Val Tyr Tyr Asn Pro Leu Trp Val His Arg Ala Ala
145                 150                 155                 160

Val Glu Asp Ala Ser Lys Thr Val Leu Gly Arg Pro Asp Val Lys Ile
                165                 170                 175

Ala Asp Leu Val Val Pro Gly Asp Phe Phe Ala Arg Asp Ile Gly Gly
            180                 185                 190

Asn Gln Leu Tyr Trp Leu Asp Val Thr Lys Ser Gly Ala Lys Glu Tyr
        195                 200                 205

Val Gln Gly Tyr Val Arg Tyr Phe Lys Asp Leu Gly Val Pro Tyr Leu
    210                 215                 220

Arg Ile Asp Phe Leu Ser Trp Tyr Glu Asp Gly Arg Asp Ala Asn Ile
225                 230                 235                 240

Gly Gln Val Asn Ala Pro His Gly Arg Ala Asn Tyr Glu Leu Ala Leu
                245                 250                 255

Ser Trp Ile Asn Glu Ala Ala Gly Glu Asp Met Glu Val Ser Leu Val
            260                 265                 270

Met Pro His Met Phe Gln Asp Gly Ser Ala Glu Leu Ala Asn Gly Asp
        275                 280                 285

Leu Val Arg Ile Asn Ala Asp Ala Asp Lys Gly Gly Trp Asp Arg Leu
    290                 295                 300
```

Ser Gly Met Arg Gln Asn Trp Gln Asp Ala Trp Pro Asn Trp Ala Asn
305                 310                 315                 320

Pro Phe Cys Gly Phe Thr Gly Trp Ser His Arg Asn Gly Arg Gly Gln
            325                 330                 335

Leu Ile Leu Asp Gly Asp Phe Met Arg Ala Ser Thr Phe Ala Ser Asp
        340                 345                 350

Glu Glu Arg Lys Thr Met Met Asn Leu Met Val Ala Ala Gly Ser Pro
    355                 360                 365

Leu Ala Ile Ala Asp Thr Tyr Gln Gln Ile Gly Asn Asn Ala Trp Val
370                 375                 380

Tyr Thr Asn Lys Glu Val Leu Gln Leu Asn Ala Asp Gly Leu Val Gly
385                 390                 395                 400

Lys Pro Leu Tyr Arg Ser Ala Thr Pro Phe Ser Lys Asp Pro Gly Ser
                405                 410                 415

Arg Asp Thr Glu Arg Trp Ala Gly Gln Leu Pro Asp Gly Ser Trp Gly
            420                 425                 430

Val Ala Leu Phe Asn Arg Ser Asp Thr Glu Thr Val Thr Lys Thr Ile
        435                 440                 445

Asp Phe Ala Lys Asp Leu Gly Leu Ala Thr Gly Gly Asn Val Arg Asp
450                 455                 460

Leu Trp Glu His Arg Asn Leu Gly Met Asp Ser Arg Ala Thr Ala Ala
465                 470                 475                 480

Leu Ala Pro His Ala Ser Ala Ile Phe Arg Val Thr Pro Pro Lys Met
                485                 490                 495

His Gly Thr Thr Arg Tyr Pro Ala Ala Phe Ala Ala Trp Gly Gly Gly
            500                 505                 510

Ala Gly Phe Asn Asn Asn His Pro Gly Tyr Asp Gly Asn Gly Phe Val
        515                 520                 525

Asp Gly Leu Gln Ala Gly Ser Gly Ser Ala Asp Pro Leu Val Thr Phe
530                 535                 540

Ala Val Gln Val Pro His Arg Gly Ser Tyr Ala Ile Arg Tyr Arg Tyr
545                 550                 555                 560

Ala Asn Ala Thr Gly Asp Thr Ser Thr Met Thr Val Thr Ala Glu Lys
                565                 570                 575

Ala Asp Arg Ser Thr Val Asp Gly Pro Val His Val Ser Phe Pro Gly
            580                 585                 590

Leu Ala Thr Trp Asp Thr Trp Gly Val Ala Asp Gly Thr Ile Thr Leu
        595                 600                 605

Asp Ala Gly Leu Asn Leu Val Thr Ile Gly Arg Gly Ala Thr Asp Lys
610                 615                 620

Gly Ala Ile Asn Leu Asn Trp Ile Glu Leu Asp Met
625                 630                 635

<210> SEQ ID NO 3
<211> LENGTH: 963
<212> TYPE: DNA
<213> ORGANISM: Chryseobacterium proteolyticum
<220> FEATURE:
<221> NAME/KEY: misc_feature
<223> OTHER INFORMATION: protein glutaminase; nucleotide sequence

<400> SEQUENCE: 3
atgaagaacc tttcctgtc catgatggcc ttcgtgaccg tcctcacctt caactcctgc    60
gccgattcca acggcaacca ggaaatcaac ggcaaggaga agctttccgt taacgattct   120
aagctgaagg atttcggcaa gaccgttccg gttggcatcg acgaagagaa cggcatgatc   180

```
aaggtgtcct tcatgttgac tgcgcagttc tacgagatca agccaaccaa ggaaaacgag    240
cagtacatcg gtatgcttcg ccaggctgtt aagaacgaat ctccagtcca cattttcctc    300
aagccaaaca gcaatgaaat cggcaaggtg gagtctgcat ccccagagga cgtccgctac    360
ttcaagacga tcctgaccaa agaagtcaag ggccagacca acaaattggc gtccgtcatt    420
ccagatgtgg ctaccctcaa ctctctcttc aaccaaatca gaaccagtc ttgcggtacc     480 tctacggcgt cctccccatg catcaccttc cgctacccag tcgacggctg ctacgcacgc    540
gcccacaaga tgcgccagat cttgatgaac aacggctatg actgtgagaa gcaattcgtg    600
tacggtaacc tcaaggcatc caccggcacc tgctgcgtgg cgtggagcta ccacgttgca    660
atcttggtga gctacaaaaa cgcttccggc gtgacggaaa acgcattat tgatccatcc     720 ctttttccca gcggtcctgt gaccgatacc gcatggcgca acgcttgcgt taacacctct    780
tgcggctctg catccgtttc tcttacgct aacaccgcag gaaatgttta ttaccgctcc     840
ccatccaatt cttacctgta tgacaacaat ctgatcaata ccaactgtgt cctgactaaa    900
ttctccctgc tttccggctg ttctccttca cctgcaccgg atgtctccag ctgtggattt    960
taa                                                                   963

<210> SEQ ID NO 4
<211> LENGTH: 320
<212> TYPE: PRT
<213> ORGANISM: Chyrseobacterium proteolyticum
<220> FEATURE:
<221> NAME/KEY: MISC_FEATURE
<223> OTHER INFORMATION: protein glutaminase; amino acid sequence

<400> SEQUENCE: 4

Met Lys Asn Leu Phe Leu Ser Met Met Ala Phe Val Thr Val Leu Thr
  1               5                  10                  15

Phe Asn Ser Cys Ala Asp Ser Asn Gly Asn Gln Glu Ile Asn Gly Lys
                 20                  25                  30

Glu Lys Leu Ser Val Asn Asp Ser Lys Leu Lys Asp Phe Gly Lys Thr
             35                  40                  45

Val Pro Val Gly Ile Asp Glu Glu Asn Gly Met Ile Lys Val Ser Phe
         50                  55                  60

Met Leu Thr Ala Gln Phe Tyr Glu Ile Lys Pro Thr Lys Glu Asn Glu
 65                  70                  75                  80

Gln Tyr Ile Gly Met Leu Arg Gln Ala Val Lys Asn Glu Ser Pro Val
                 85                  90                  95

His Ile Phe Leu Lys Pro Asn Ser Asn Glu Ile Gly Lys Val Glu Ser
                100                 105                 110

Ala Ser Pro Glu Asp Val Arg Tyr Phe Lys Thr Ile Leu Thr Lys Glu
            115                 120                 125

Val Lys Gly Gln Thr Asn Lys Leu Ala Ser Val Ile Pro Asp Val Ala
        130                 135                 140

Thr Leu Asn Ser Leu Phe Asn Gln Ile Lys Asn Gln Ser Cys Gly Thr
145                 150                 155                 160

Ser Thr Ala Ser Ser Pro Cys Ile Thr Phe Arg Tyr Pro Val Asp Gly
                165                 170                 175

Cys Tyr Ala Arg Ala His Lys Met Arg Gln Ile Leu Met Asn Asn Gly
            180                 185                 190

Tyr Asp Cys Glu Lys Gln Phe Val Tyr Gly Asn Leu Lys Ala Ser Thr
        195                 200                 205

Gly Thr Cys Cys Val Ala Trp Ser Tyr His Val Ala Ile Leu Val Ser
```

```
            210                 215                 220
Tyr Lys Asn Ala Ser Gly Val Thr Glu Lys Arg Ile Ile Asp Pro Ser
225                 230                 235                 240

Leu Phe Ser Ser Gly Pro Val Thr Asp Thr Ala Trp Arg Asn Ala Cys
                245                 250                 255

Val Asn Thr Ser Cys Gly Ser Ala Ser Val Ser Ser Tyr Ala Asn Thr
            260                 265                 270

Ala Gly Asn Val Tyr Tyr Arg Ser Pro Ser Asn Ser Tyr Leu Tyr Asp
        275                 280                 285

Asn Asn Leu Ile Asn Thr Asn Cys Val Leu Thr Lys Phe Ser Leu Leu
    290                 295                 300

Ser Gly Cys Ser Pro Ser Pro Ala Pro Asp Val Ser Ser Cys Gly Phe
305                 310                 315                 320

<210> SEQ ID NO 5
<211> LENGTH: 90
<212> TYPE: DNA
<213> ORGANISM: Arthrobacter globiformis
<220> FEATURE:
<221> NAME/KEY: misc_feature
<223> OTHER INFORMATION: IMD signal sequence; nucleotide sequence

<400> SEQUENCE: 5
atgatgaacc tgtcccgccg cacattgctc accaccggca gcgccgccac cctcgcctac      60
gccttgggca tggcaggctc cgcccaggcc                                      90

<210> SEQ ID NO 6
<211> LENGTH: 30
<212> TYPE: PRT
<213> ORGANISM: Arthrobacter globiformis
<220> FEATURE:
<221> NAME/KEY: MISC_FEATURE
<223> OTHER INFORMATION: IMD signal peptide

<400> SEQUENCE: 6

Met Met Asn Leu Ser Arg Arg Thr Leu Leu Thr Thr Gly Ser Ala Ala
1               5                   10                  15

Thr Leu Ala Tyr Ala Leu Gly Met Ala Gly Ser Ala Gln Ala
            20                  25                  30

<210> SEQ ID NO 7
<211> LENGTH: 117
<212> TYPE: DNA
<213> ORGANISM: Escherichia coli
<220> FEATURE:
<221> NAME/KEY: misc_feature
<223> OTHER INFORMATION: TorA signal sequence; nucleotide sequence

<400> SEQUENCE: 7
atgaacaata cgatctcttt caggcatca cgtcggcgtt ttctggcaca actcggcggc       60
ttaaccgtcg ccgggatgct ggggccgtca ttgttaacgc cgcgacgtgc gactgcg       117

<210> SEQ ID NO 8
<211> LENGTH: 39
<212> TYPE: PRT
<213> ORGANISM: Escherichia coli
<220> FEATURE:
<221> NAME/KEY: MISC_FEATURE
<223> OTHER INFORMATION: TorA signal peptide

<400> SEQUENCE: 8

Met Asn Asn Asn Asp Leu Phe Gln Ala Ser Arg Arg Arg Phe Leu Ala
1               5                   10                  15
```

Gln Leu Gly Gly Leu Thr Val Ala Gly Met Leu Gly Pro Ser Leu Leu
            20                  25                  30

Thr Pro Arg Arg Ala Thr Ala
            35

<210> SEQ ID NO 9
<211> LENGTH: 945
<212> TYPE: DNA
<213> ORGANISM: Corynebacterium glutamicum
<220> FEATURE:
<221> NAME/KEY: misc_feature
<223> OTHER INFORMATION: tatC gene sequence

<400> SEQUENCE: 9
atgtccattg ttgagcacat caaagagttt cgacgccgac ttcttatcgc tctggcgggc      60
atcctcgtgg gcaccattat cggctttatt tggtacgatt tctcattttg gcagatcccc     120
actttgggcg agctgctgag ggatccgtac tgttctctgc ctgctgaatc ccgctgggcc     180
atgagcgact cagaggaatg tcgactgctc gcaaccggcc cgtttgatcc attcatgctt     240
cgccttaaag tagcggcgtt ggtgggtatg gttcttggct cacccgtgtg gctgagccag     300
ctgtggggct ttatcacccc aggtttgatg aagaatgagc gccgttacac cgcaatcttc     360
gtcacgattg ctgttgtgct gtttgtcggc ggtgctgttc ttgcgtactt cgtcgttgca     420
tatggtttgg agttcctcct taccattggt ggagacaccc aggcagcggc cctgactggt     480
gataagtact tcggattctt gctcgcgttg ttggcgattt tcggcgtgag cttcgaagtt     540
ccactggtga tcggcatgct caacattgtg ggtatcttgc cttacgatgc cattaaagat     600
aagcgacgca tgatcatcat gattttgttc gtgttcgctg cttcatgac acccggccag     660 gatcctttca ccatgttggt gttggcgctt tcactcaccg ttctggtaga gcttgccctg     720
cagttctgtc gtttcaacga caaacgccgg gacaagaagc gcccagaatg gcttgatggc     780
gatgacctct ctgcatcacc actggatact ctgctggtg gagaagatgc tccaagccca     840
gtcgaaaccc cagaggcggt ggagccttcg cggatgctga acccaagtgg ggaggcgtcg     900
ataagctata aacccggggcg cgccgacttc ggtgacgtgc tctag                    945

<210> SEQ ID NO 10
<211> LENGTH: 314
<212> TYPE: PRT
<213> ORGANISM: Corynebacterium glutamicum
<220> FEATURE:
<221> NAME/KEY: MISC_FEATURE
<223> OTHER INFORMATION: tatC amino acid sequence

<400> SEQUENCE: 10

Met Ser Ile Val Glu His Ile Lys Glu Phe Arg Arg Arg Leu Leu Ile
1               5                   10                  15

Ala Leu Ala Gly Ile Leu Val Gly Thr Ile Ile Gly Phe Ile Trp Tyr
            20                  25                  30

Asp Phe Ser Phe Trp Gln Ile Pro Thr Leu Gly Glu Leu Leu Arg Asp
        35                  40                  45

Pro Tyr Cys Ser Leu Pro Ala Glu Ser Arg Trp Ala Met Ser Asp Ser
    50                  55                  60

Glu Glu Cys Arg Leu Leu Ala Thr Gly Pro Phe Asp Pro Phe Met Leu
65                  70                  75                  80

Arg Leu Lys Val Ala Ala Leu Val Gly Met Val Leu Gly Ser Pro Val
                85                  90                  95

Trp Leu Ser Gln Leu Trp Gly Phe Ile Thr Pro Gly Leu Met Lys Asn

-continued

```
            100                 105                 110
Glu Arg Arg Tyr Thr Ala Ile Phe Val Thr Ile Ala Val Val Leu Phe
        115                 120                 125

Val Gly Gly Ala Val Leu Ala Tyr Phe Val Val Ala Tyr Gly Leu Glu
    130                 135                 140

Phe Leu Leu Thr Ile Gly Gly Asp Thr Gln Ala Ala Ala Leu Thr Gly
145                 150                 155                 160

Asp Lys Tyr Phe Gly Phe Leu Ala Leu Ala Ile Phe Gly Val
                165                 170                 175

Ser Phe Glu Val Pro Leu Val Ile Gly Met Leu Asn Ile Val Gly Ile
            180                 185                 190

Leu Pro Tyr Asp Ala Ile Lys Asp Lys Arg Arg Met Ile Ile Met Ile
        195                 200                 205

Leu Phe Val Phe Ala Ala Phe Met Thr Pro Gly Gln Asp Pro Phe Thr
    210                 215                 220

Met Leu Val Leu Ala Leu Ser Leu Thr Val Leu Val Glu Leu Ala Leu
225                 230                 235                 240

Gln Phe Cys Arg Phe Asn Asp Lys Arg Arg Asp Lys Lys Arg Pro Glu
                245                 250                 255

Trp Leu Asp Gly Asp Asp Leu Ser Ala Ser Pro Leu Asp Thr Ser Ala
            260                 265                 270

Gly Gly Glu Asp Ala Pro Ser Pro Val Glu Thr Pro Glu Ala Val Glu
        275                 280                 285

Pro Ser Arg Met Leu Asn Pro Ser Gly Glu Ala Ser Ile Ser Tyr Lys
    290                 295                 300

Pro Gly Arg Ala Asp Phe Gly Asp Val Leu
305                 310

<210> SEQ ID NO 11
<211> LENGTH: 20
<212> TYPE: DNA
<213> ORGANISM: Artificial Sequence
<220> FEATURE:
<223> OTHER INFORMATION: synthetic olygonucleotide

<400> SEQUENCE: 11
atgatgaacc tgtcccgccg                                            20

<210> SEQ ID NO 12
<211> LENGTH: 23
<212> TYPE: DNA
<213> ORGANISM: Artificial Sequence
<220> FEATURE:
<223> OTHER INFORMATION: synthetic olygonucleotide

<400> SEQUENCE: 12
cgcggatccc tgagggcggg aac                                        23

<210> SEQ ID NO 13
<211> LENGTH: 20
<212> TYPE: DNA
<213> ORGANISM: Artificial Sequence
<220> FEATURE:
<223> OTHER INFORMATION: synthetic olygonucleotide

<400> SEQUENCE: 13
gtccccgtca cggccgcgcc                                            20

<210> SEQ ID NO 14
<211> LENGTH: 26
```

```
<212> TYPE: DNA
<213> ORGANISM: Artificial Sequence
<220> FEATURE:
<223> OTHER INFORMATION: synthetic olygonucleotide

<400> SEQUENCE: 14
aaattcctgt gaattagctg atttag                                          26

<210> SEQ ID NO 15
<211> LENGTH: 46
<212> TYPE: DNA
<213> ORGANISM: Artificial Sequence
<220> FEATURE:
<223> OTHER INFORMATION: synthetic olygonucleotide

<400> SEQUENCE: 15
cccgggcggg cggtgacggc ggtggctgcc gttgccacag gtgcgg                    46

<210> SEQ ID NO 16
<211> LENGTH: 39
<212> TYPE: DNA
<213> ORGANISM: Artificial Sequence
<220> FEATURE:
<223> OTHER INFORMATION: synthetic olygonucleotide

<400> SEQUENCE: 16
ggcgggacag gttcatcata gaggcgaagg ctccttgaa                            39

<210> SEQ ID NO 17
<211> LENGTH: 21
<212> TYPE: DNA
<213> ORGANISM: Artificial Sequence
<220> FEATURE:
<223> OTHER INFORMATION: synthetic olygonucleotide

<400> SEQUENCE: 17
catgaagaac cttttcctgt c                                               21

<210> SEQ ID NO 18
<211> LENGTH: 26
<212> TYPE: DNA
<213> ORGANISM: Artificial Sequence
<220> FEATURE:
<223> OTHER INFORMATION: synthetic olygonucleotide

<400> SEQUENCE: 18
gtaaaaggat ccattaatta aaatcc                                          26

<210> SEQ ID NO 19
<211> LENGTH: 40
<212> TYPE: DNA
<213> ORGANISM: Artificial Sequence
<220> FEATURE:
<223> OTHER INFORMATION: synthetic olygonucleotide

<400> SEQUENCE: 19
tcctggttgc cgttggaatc tgccgttgcc acaggtgcgg                           40

<210> SEQ ID NO 20
<211> LENGTH: 20
<212> TYPE: DNA
<213> ORGANISM: Artificial Sequence
<220> FEATURE:
<223> OTHER INFORMATION: synthetic olygonucleotide

<400> SEQUENCE: 20
gattccaacg gcaaccagga                                                 20
```

<210> SEQ ID NO 21
<211> LENGTH: 38
<212> TYPE: DNA
<213> ORGANISM: Artificial Sequence
<220> FEATURE:
<223> OTHER INFORMATION: synthetic olygonucleotide

<400> SEQUENCE: 21
cctggttgcc gttggaatcg gcctgggcgg agcctgcc                                38

<210> SEQ ID NO 22
<211> LENGTH: 25
<212> TYPE: DNA
<213> ORGANISM: Artificial Sequence
<220> FEATURE:
<223> OTHER INFORMATION: synthetic olygonucleotide

<400> SEQUENCE: 22
atgaacaata acgatctctt tcagg                                              25

<210> SEQ ID NO 23
<211> LENGTH: 26
<212> TYPE: DNA
<213> ORGANISM: Artificial Sequence
<220> FEATURE:
<223> OTHER INFORMATION: synthetic olygonucleotide

<400> SEQUENCE: 23
ccggatcctg gtcatgattt cacctg                                             26

<210> SEQ ID NO 24
<211> LENGTH: 43
<212> TYPE: DNA
<213> ORGANISM: Artificial Sequence
<220> FEATURE:
<223> OTHER INFORMATION: synthetic olygonucleotide

<400> SEQUENCE: 24
aagagatcgt tattgttcat agaggcgaag gctccttgaa tag                          43

<210> SEQ ID NO 25
<211> LENGTH: 44
<212> TYPE: DNA
<213> ORGANISM: Artificial Sequence
<220> FEATURE:
<223> OTHER INFORMATION: synthetic olygonucleotide

<400> SEQUENCE: 25
gatttcctgg ttgccgttgg aatccgcagt cgcacgtcgc ggcg                         44

<210> SEQ ID NO 26
<211> LENGTH: 34
<212> TYPE: DNA
<213> ORGANISM: Artificial Sequence
<220> FEATURE:
<223> OTHER INFORMATION: synthetic olygonucleotide

<400> SEQUENCE: 26
ggcggtaccg ttaagcgccc tcggcgagtt atct                                    34

<210> SEQ ID NO 27
<211> LENGTH: 34
<212> TYPE: DNA
<213> ORGANISM: Artificial Sequence
<220> FEATURE:
<223> OTHER INFORMATION: synthetic olygonucleotide

```
<400> SEQUENCE: 27
gcctctagac tagagcacgt caccgaagtc ggcg                                    34

<210> SEQ ID NO 28
<211> LENGTH: 27
<212> TYPE: PRT
<213> ORGANISM: Escherichia coli
<220> FEATURE:
<221> NAME/KEY: MISC_FEATURE
<223> OTHER INFORMATION: SufI signal peptide

<400> SEQUENCE: 28

Met Ser Leu Ser Arg Arg Gln Phe Ile Gln Ala Ser Gly Ile Ala Leu
1               5                   10                  15

Cys Ala Gly Ala Val Pro Leu Lys Ala Ser Ala
            20                  25

<210> SEQ ID NO 29
<211> LENGTH: 48
<212> TYPE: PRT
<213> ORGANISM: Bacillus subtilis
<220> FEATURE:
<221> NAME/KEY: MISC_FEATURE
<223> OTHER INFORMATION: PhoD signal peptide

<400> SEQUENCE: 29

Met Ala Tyr Asp Ser Arg Phe Asp Glu Trp Val Gln Lys Leu Lys Glu
1               5                   10                  15

Glu Ser Phe Gln Asn Asn Thr Phe Asp Arg Arg Lys Phe Ile Gln Gly
            20                  25                  30

Ala Gly Lys Ile Ala Gly Leu Ser Leu Gly Leu Thr Ile Ala Gln Ser
        35                  40                  45

<210> SEQ ID NO 30
<211> LENGTH: 34
<212> TYPE: PRT
<213> ORGANISM: Bacillus subtilis
<220> FEATURE:
<221> NAME/KEY: MISC_FEATURE
<223> OTHER INFORMATION: LipA signal peptide

<400> SEQUENCE: 30

Met Lys Phe Val Lys Arg Arg Thr Thr Ala Leu Val Thr Thr Leu Met
1               5                   10                  15

Leu Ser Val Thr Ser Leu Phe Ala Leu Gln Pro Ser Ala Lys Ala Ala
            20                  25                  30

Glu His

<210> SEQ ID NO 31
<211> LENGTH: 6
<212> TYPE: PRT
<213> ORGANISM: Artificial sequence
<220> FEATURE:
<223> OTHER INFORMATION: tatC dependent signal petide motif
<220> FEATURE:
<221> NAME/KEY: MISC_FEATURE
<222> LOCATION: (1)..(1)
<223> OTHER INFORMATION: Ser or Thr
<220> FEATURE:
<221> NAME/KEY: MISC_FEATURE
<222> LOCATION: (3)..(3)
<223> OTHER INFORMATION: any amino acid

<400> SEQUENCE: 31

Xaa Arg Xaa Phe Leu Lys
```

<210> SEQ ID NO 32
<211> LENGTH: 5
<212> TYPE: PRT
<213> ORGANISM: Artificial sequence
<220> FEATURE:
<223> OTHER INFORMATION: tatC depedent signal peptide motif
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: hydrophobic amino acid
<220> FEATURE:
<221> NAME/KEY: MISC_FEATURE
<222> LOCATION: (5)..(5)
<223> OTHER INFORMATION: hydrophobic amino acid

<400> SEQUENCE: 32

Arg Arg Xaa Xaa Xaa
1               5

<210> SEQ ID NO 33
<211> LENGTH: 20
<212> TYPE: DNA
<213> ORGANISM: Artificial
<220> FEATURE:
<223> OTHER INFORMATION: synthetic olygonucleotide

<400> SEQUENCE: 33
gcttgatcat cctttaagg                                          20

<210> SEQ ID NO 34
<211> LENGTH: 40
<212> TYPE: DNA
<213> ORGANISM: Artificial
<220> FEATURE:
<223> OTHER INFORMATION: synthetic olygonucleotide

<400> SEQUENCE: 34
atgtgctcaa caatggacat gtggtctact ccaaattcac                   40

<210> SEQ ID NO 35
<211> LENGTH: 945
<212> TYPE: DNA
<213> ORGANISM: Corynebacterium glutamicum
<220> FEATURE:
<221> NAME/KEY: misc_feature
<223> OTHER INFORMATION: tatC gene sequence

<400> SEQUENCE: 35
atgtccattg ttgagcacat caaagagttt cgacgccgac ttctcatcgc tctggcgggc    60
atcctcgtgg gcaccattat cggctttatt tggtacgatt tctcattttg cagatcccc    120 actttgggcg agctgctgag ggatccgtac tgttctttgc ctgctgaatc ccgctgggcc    180
atgagcgact cagaggaatg tcgactgctc gcaaccggcc cgtttgatcc attcatgctt    240
cgccttaaag tagcggcgtt ggtgggtatg gttcttggct cacccgtgtg gctgagccag    300
ctgtggggct ttatcacccc aggtttgatg aagaatgagc gccgttacac cgcaatcttc    360
gtcacgattg ctgttgtgct gtttgtcggc ggtgctgttc ttgcgtactt cgtcgttgca    420
tatggtttgg agttcctcct taccattggt ggagacaccc aggcagcggc cctgactggt    480
gataagtact tcggattctt gctcgcgttg ttggcgattt cggcgtgag cttcgaagtt    540

```
ccactggtga tcggcatgct caacattgtg gtatcttgc cctacgatgc cattaaagat       600
aagcgacgca tgatcatcat gattttgttc gtgttcgctg ctttcatgac acccggccag      660
gatcctttca ccatgttggt gttggcgctt tcactcaccg ttctggtgga gcttgccctg      720
cagttctgtc gcttcaacga caaacgccgg gacaagaagc gcccagaatg gcttgatggc      780
gatgacctct ctgcatcacc actggatact tctgctggtg gagaagatgc tccaagccca      840
gtcgaaaccc cagaggcggt ggagccttcg cggatgctga acccaagtgg ggaggcgtcg      900
ataagctata aacccgggcg cgccgacttc ggtgacgtgc tctag                      945
```

<210> SEQ ID NO 36
<211> LENGTH: 21
<212> TYPE: DNA
<213> ORGANISM: Artificial
<220> FEATURE:
<223> OTHER INFORMATION: synthetic olygonucleotide

<400> SEQUENCE: 36

```
atgtccattg ttgagcacat c                                                 21
```

<210> SEQ ID NO 37
<211> LENGTH: 20
<212> TYPE: DNA
<213> ORGANISM: Artificial
<220> FEATURE:
<223> OTHER INFORMATION: synthetic olygonucleotide

<400> SEQUENCE: 37

```
ctagagcacg tcaccgaagt                                                   20
```

<210> SEQ ID NO 38
<211> LENGTH: 2402
<212> TYPE: DNA
<213> ORGANISM: Artificial
<220> FEATURE:
<223> OTHER INFORMATION: tatA+tatC

<400> SEQUENCE: 38

```
gcttgatcat tcctttaagg aagtaaaaat ccacaatgct caaggcatgg ataaacccct       60
gcgcctcaca ccaactgaag ccggtgtttt gctgctgaca cttgaatccc tggaatccct      120
ccccggtatt gcgaaacagg aagcggtcgt atctgctgcg aacaagctac gcgccatcat      180
gggagagtat tcctcgactg ttttcgactc cactggagaa gacctcgacg ctgaagttct      240
agagatcatc cgcgacgcca tggatttaca ccagcaggtc agttttgaat accactcgca      300
cagatcagac aacaccagcc tgaggcaagt cagccctgct catatcttca cccatgaagg      360
cgaaacctac atcaaagcct gggaagaagc tgtgaaacaa tggcggacgt ttaggcttga      420
tcgcatccga agcattgtgc ttcttgacag caaagcagtg cacccggcgc gaggggtttc      480
agtatccacg gacgatcctt ttgagttcgc aaaatcttcc gatattgcca cgttattgct      540
acgtgaggac gcaatgtggt taggcaatta catggccatg gaggtggatg aaacggtgga      600
accgattcgc gatagcgacg gattcagctg gcacacagtc cactttccgc tgctttctag      660
ggattggttc gtccgattcg cgattggcca tgctgagcat ttgaaagtaa ctagtcccga      720
agatcttcgg aaatgcataa agcaaaaggc tcttagtggt ttgtcagcgt atgatcatca      780
cgtagagtaa cacccaagag taagacgcaa catcaatcaa tgtgcaaggg tttcattct      840 ggaaatcgtg gtcaccccac attccagt catggacaag cttgttttaat gtgaatttgg        900 agtagaccac atgcccactc tcggaccatg ggaaatcgcg atcattgtcc tgctgatcat      960
```

```
tctgctgttc ggcgcgaaga agctgcctga tgcagctcgt tccatcggcc gttccatgcg   1020
catcttcaag tctgaagtca agaaatgaa caaggacggc gataccccag aacaacaaca    1080
gcagcagcct cagcagcagc agcagattgc gcccaaccag atcgaggctc ctcagccagt   1140
tcagcagcca gcgcaacagt caaactttga gcagcactac cagggccagc aggttcagca   1200
gcctcagaac cctcagaccc ctgactaccg tcagaactac gaggatccaa accgcacctc   1260
ctaaagttgg gcagtttgca tctaaaaaat aaagtcatcg caccgtaaca gctacctttt   1320
gttgcggtgc gtcgtagtct gtacataaaa acgcaggtag gacgttcaag gaattggctg   1380
aatcaacaag cgccaaggtg gttaagcgcc ctcggcgagt tatctcagaa agaagaaga   1440 agtctcctac gggagagatg tccattgttg agcacatcaa agagtttcga cgccgacttc   1500
tcatcgctct ggcgggcatc ctcgtgggca ccattatcgg cttatttgg tacgatttct    1560 cattttggca gatccccact ttgggcgagc tgctgaggga tccgtactgt tctttgcctg   1620
ctgaatcccg ctgggccatg agcgactcag aggaatgtcg actgctcgca accggcccgt   1680
ttgatccatt catgcttcgc cttaaagtag cggcgttggt gggtatggtt cttggctcac   1740
ccgtgtggct gagccagctg tggggcttta tcaccccagg tttgatgaag aatgagcgcc   1800
gttacaccgc aatcttcgtc acgattgctg ttgtgctgtt tgtcggcggt gctgttcttg   1860
cgtacttcgt cgttgcatat ggtttggagt tcctccttac cattggtgga gacacccagg   1920
cagcggccct gactggtgat aagtacttcg gattcttgct cgcgttgttg gcgattttcg   1980
gcgtgagctt cgaagttcca ctggtgatcg gcatgctcaa cattgtgggt atcttgccct   2040
acgatgccat taaagataag cgacgcatga tcatcatgat tttgttcgtg ttcgctgctt   2100
tcatgacacc cggccaggat cctttcacca tgttggtgtt ggcgctttca ctcaccgttc   2160
tggtggagct tgccctgcag ttctgtcgct tcaacgacaa acgccgggac aagaagcgcc   2220
cagaatggct tgatggcgat gacctctctg catcaccact ggatacttct gctggtggag   2280
aagatgctcc aagcccagtc gaaacccccag aggcggtgga gccttcgcgg atgctgaacc   2340
caagtgggga ggcgtcgata agctataaac ccgggcgcgc cgacttcggt gacgtgctct   2400
ag                                                                  2402

<210> SEQ ID NO 39
<211> LENGTH: 20
<212> TYPE: DNA
<213> ORGANISM: artificial
<220> FEATURE:
<223> OTHER INFORMATION: synthetic olygonucleotide

<400> SEQUENCE: 39
gaggcgctgc ctgaagatta                                               20

<210> SEQ ID NO 40
<211> LENGTH: 20
<212> TYPE: DNA
<213> ORGANISM: artificial
<220> FEATURE:
<223> OTHER INFORMATION: synthetic olygonucleotide

<400> SEQUENCE: 40
gacaggtgaa gaggtcaagg                                               20

<210> SEQ ID NO 41
<211> LENGTH: 1710
<212> TYPE: DNA
<213> ORGANISM: Corynebacterium glutamicum
<220> FEATURE:
```

<221> NAME/KEY: misc_feature
<223> OTHER INFORMATION: tatB gene sequence

<400> SEQUENCE: 41

```
gaggcgctgc ctgaagatta tgagcgcgtt ccgggcaatg acatcacccc agagcaggca      60
tacaccgaag ctcaccttga cccagctctg caggcagccc tcgatgagtt gagcccagac     120
ttccgcgtgg ccgtgatcct gtgtgacgtt gttggtatga gctatgacga aatcgcagag     180
accctcggag tgaagatggg taccgtgcgt tcccgtattc accgtggacg cagccagctt     240
cgtgcaagtt tggaagctgc agcaatgacc agcgaggaag tttctttgtt ggtcccaacc     300
cactaaagct ggtgtgtttt ctgacacgac aaacgcaaat gtcgtgtcat ttttgcagct     360
cagtgcatta ttttggggtt cgtggtgcgg cagggaact tatcgcaggc gacatccgtt      420
ttgagtagta ggtatcttgg ataagaagtt acccacatcc ttgaaagtcg agacacagga     480
ggtcatcgga agatatgttc aattccgaca ccaccgcgaa tctccaagct aaaagtcgag     540
atcgtgcagg atctaaagca aagcgcagca ggccaagttt tgattcagta gcgcgggatg     600
ttttggatgt tcgaacaaaa acagcacaag ttaaaaacaa ggctaaagag ttttcctctg     660
ttgatcacct ttcagcagac gccgcagcca tgtttgtaga caatgaactg tcccgtggcg     720
ccatgcatcg cgccaggctg cacattgtgc actgcgctga atgtagggaa gagattaacc     780
gtcagcagga aaccgtcgat tatctccgct cagagtgcaa aaacgaagaa gtgtccgccc     840
caatggacct caaagcacgg cttgccagcc tcgccactga gtgcatgcct ggccctggcg     900
cagagaattt agcaatgcag cgcccagagt cttttgtggc taaagttgag tccgtagtgc     960
gcgcagttcg taagaaccaa ggccgctaat ttttaatcct tatttacatt ttctgtgaca    1020
ttctctgaaa gaccggtctg atgttttcta gcgtgggttg gggagagatc ttcctcttag    1080
tcgttgtggg ccttgttgtc atcggcccgg aacggttgcc tcgtttgatc caggacgcac    1140
gcgctgcgct gctcgctgca cgtaccgcta tcgacaatgc aaagcagtcg ttggacagtg    1200
attttggttc ggaatttgat gaaatccgaa agccactaac ccaggttgca cagtacagcc    1260
ggatgagccc caagacggcc atcactaagg cgttgtttga taatgattcc tcgttcctgg    1320
atgactttga tccaaagaag atcatggccg aaggaacaga aggcgaagct cagcgccaca    1380
agcaggcagc tgacaacaat gcgaatgtgg tggaacgtcc agctgatggt tccaccgcac    1440
gcccaacgca aaacgatcca aaagacggcc cgaattactc aggcggcgtc tcttggaccg    1500
atattattta gcttttattt aacgccaagc ccaagcgttt tacccaccag cgataccttg    1560
cggtgggcta ggtgttcagc gatctcattg atcgctgcag cggttgggga gtgtggttca    1620
gaaatcgcaa taggatttcc cacatcgcca ccgatacgca ggttcggatc caatggaaca    1680
gatccgatga ccttgacctc ttcacctgtc                                    1710
```

<210> SEQ ID NO 42
<211> LENGTH: 41
<212> TYPE: DNA
<213> ORGANISM: Artificial
<220> FEATURE:
<223> OTHER INFORMATION: synthetic olygonucleotide, primer

<400> SEQUENCE: 42

```
gtctcttccc ccgcgccatt gtcggcctgg gcggagcctg c                         41
```

<210> SEQ ID NO 43
<211> LENGTH: 19
<212> TYPE: DNA
<213> ORGANISM: artificial

-continued

```
<220> FEATURE:
<223> OTHER INFORMATION: synthetic olygonucleotide, primer

<400> SEQUENCE: 43
gacaatggcg cggggggaag                                                        19

<210> SEQ ID NO 44
<211> LENGTH: 28
<212> TYPE: DNA
<213> ORGANISM: artificial
<220> FEATURE:
<223> OTHER INFORMATION: synthetic olygonucleotide, primer

<400> SEQUENCE: 44
cgctcacatc acggccagcc ctgcttta                                               28

<210> SEQ ID NO 45
<211> LENGTH: 39
<212> TYPE: DNA
<213> ORGANISM: artificial
<220> FEATURE:
<223> OTHER INFORMATION: primer

<400> SEQUENCE: 45 cttccccgc gccattgtcc gcagtcgcac gtcgcggcg                                    39

<210> SEQ ID NO 46
<211> LENGTH: 117
<212> TYPE: PRT
<213> ORGANISM: Corynebacterium glutamicum
<220> FEATURE:
<221> NAME/KEY: MISC_FEATURE
<223> OTHER INFORMATION: tatA amino acid sequence

<400> SEQUENCE: 46
```

Met Pro Thr Leu Gly Pro Trp Glu Ile Ala Ile Ile Val Leu Leu Ile
1               5                   10                  15

Ile Leu Leu Phe Gly Ala Lys Lys Leu Pro Asp Ala Ala Arg Ser Ile
            20                  25                  30

Gly Arg Ser Met Arg Ile Phe Lys Ser Glu Val Lys Glu Met Asn Lys
        35                  40                  45

Asp Gly Asp Thr Pro Glu Gln Gln Gln Gln Pro Gln Gln Gln Gln
    50                  55                  60

Gln Ile Ala Pro Asn Gln Ile Glu Ala Pro Gln Pro Val Gln Gln Pro
65                  70                  75                  80

Ala Gln Gln Ser Asn Phe Glu Gln His Tyr Gln Gly Gln Val Gln
                85                  90                  95

Gln Pro Gln Asn Pro Gln Thr Pro Asp Tyr Arg Gln Asn Tyr Glu Asp
            100                 105                 110

Pro Asn Arg Thr Ser
        115

```
<210> SEQ ID NO 47
<211> LENGTH: 157
<212> TYPE: PRT
<213> ORGANISM: Corynebacterium glutamicum
<220> FEATURE:
<221> NAME/KEY: MISC_FEATURE
<223> OTHER INFORMATION: tatB amino acid sequence

<400> SEQUENCE: 47
```

Met Phe Ser Ser Val Gly Trp Gly Glu Ile Phe Leu Leu Val Val Val
1               5                   10                  15

Gly Leu Val Val Ile Gly Pro Glu Arg Leu Pro Arg Leu Ile Gln Asp
            20                  25                  30

Ala Arg Ala Ala Leu Leu Ala Ala Arg Thr Ala Ile Asp Asn Ala Lys
            35                  40                  45

Gln Ser Leu Asp Ser Asp Phe Gly Ser Glu Phe Asp Glu Ile Arg Lys
 50                  55                  60

Pro Leu Thr Gln Val Ala Gln Tyr Ser Arg Met Ser Pro Lys Thr Ala
 65                  70                  75                  80

Ile Thr Lys Ala Leu Phe Asp Asn Asp Ser Ser Phe Leu Asp Asp Phe
                    85                  90                  95

Asp Pro Lys Lys Ile Met Ala Glu Gly Thr Glu Gly Glu Ala Gln Arg
            100                 105                 110

His Lys Gln Ala Ala Asp Asn Asn Ala Asn Val Val Glu Arg Pro Ala
            115                 120                 125

Asp Gly Ser Thr Ala Arg Pro Thr Gln Asn Asp Pro Lys Asp Gly Pro
130                 135                 140

Asn Tyr Ser Gly Gly Val Ser Trp Thr Asp Ile Ile Leu
145                 150                 155

<210> SEQ ID NO 48
<211> LENGTH: 225
<212> TYPE: DNA
<213> ORGANISM: Corynebacterium glutamicum
<220> FEATURE:
<221> NAME/KEY: misc_feature
<223> OTHER INFORMATION: tatE gene sequence

<400> SEQUENCE: 48
atgacgcctg caggtccagc acaattactc attgttgctc ttgtagtaat tgtcctcttt      60
ggttctaata agttgcctga tgttgctcgg tccgttggcc gttcgatgcg cattttcaaa     120
tctgagatca aagagatgaa caaggatcag atcgaaagct ccgatcagac cttgaagaac     180
taaggttcct cgcatctaaa aaaccgcct gccttctctg tttag                      225

<210> SEQ ID NO 49
<211> LENGTH: 60
<212> TYPE: PRT
<213> ORGANISM: Corynebacterium glutamicum
<220> FEATURE:
<221> NAME/KEY: MISC_FEATURE
<223> OTHER INFORMATION: tatE amino acid sequence

<400> SEQUENCE: 49

Met Thr Pro Ala Gly Pro Ala Gln Leu Leu Ile Val Ala Leu Val Val
 1               5                   10                  15

Ile Val Leu Phe Gly Ser Asn Lys Leu Pro Asp Val Ala Arg Ser Val
            20                  25                  30

Gly Arg Ser Met Arg Ile Phe Lys Ser Glu Ile Lys Glu Met Asn Lys
            35                  40                  45

Asp Gln Ile Glu Ser Ser Asp Gln Thr Leu Lys Asn
 50                  55                  60

<210> SEQ ID NO 50
<211> LENGTH: 33
<212> TYPE: DNA
<213> ORGANISM: Artificial
<220> FEATURE:
<223> OTHER INFORMATION: synthetic olygonucleotide, primer, for FGPK

<400> SEQUENCE: 50
cttggggccg aagcccttga cttctttggt cag                                   33

<210> SEQ ID NO 51
<211> LENGTH: 33
<212> TYPE: DNA
<213> ORGANISM: Artificial
<220> FEATURE:
<223> OTHER INFORMATION: synthetic olygonucleotide, primer, for FGPK

<400> SEQUENCE: 51
ttcggcccca agttggcgtc cgtcattcca gat                                    33

<210> SEQ ID NO 52
<211> LENGTH: 33
<212> TYPE: DNA
<213> ORGANISM: Artificial
<220> FEATURE:
<223> OTHER INFORMATION: synthetic olygonucleotide, primer for FGPF

<400> SEQUENCE: 52 gaagggccg aagcccttga cttctttggt cag                                     33

<210> SEQ ID NO 53
<211> LENGTH: 33
<212> TYPE: DNA
<213> ORGANISM: artificial
<220> FEATURE:
<223> OTHER INFORMATION: synthetic olygonucleotide, primer for FGPF

<400> SEQUENCE: 53
ttcggcccct tcttggcgtc cgtcattcca gat                                    33

<210> SEQ ID NO 54
<211> LENGTH: 33
<212> TYPE: DNA
<213> ORGANISM: Artificial
<220> FEATURE:
<223> OTHER INFORMATION: synthetic olygonucleotide, primer for FAPF

<400> SEQUENCE: 54
gaagggcgcg aagcccttga cttctttggt cag                                    33

<210> SEQ ID NO 55
<211> LENGTH: 33
<212> TYPE: DNA
<213> ORGANISM: Artificial
<220> FEATURE:
<223> OTHER INFORMATION: synthetic olygonucleotide, primer for FAPF

<400> SEQUENCE: 55
ttcgcgccct tcttggcgtc cgtcattcca gat                                    33

<210> SEQ ID NO 56
<211> LENGTH: 33
<212> TYPE: DNA
<213> ORGANISM: Artificial
<220> FEATURE:
<223> OTHER INFORMATION: synthetic olygonucleotide, primer for FAPY

<400> SEQUENCE: 56
gtagggcgcg aagcccttga cttctttggt cag                                    33

<210> SEQ ID NO 57
<211> LENGTH: 33
<212> TYPE: DNA
<213> ORGANISM: Artificial
<220> FEATURE:
<223> OTHER INFORMATION: synthetic olygonucleotide, primer for FAPY

<400> SEQUENCE: 57
ttcgcgccct acttggcgtc cgtcattcca gat            33

<210> SEQ ID NO 58
<211> LENGTH: 33
<212> TYPE: DNA
<213> ORGANISM: Artificial
<220> FEATURE:
<223> OTHER INFORMATION: synthetic olygonucleotide, primer for AHAY

<400> SEQUENCE: 58
gtacgcgtgc gcgcccttga cttctttggt cag            33

<210> SEQ ID NO 59
<211> LENGTH: 33
<212> TYPE: DNA
<213> ORGANISM: Artificial
<220> FEATURE:
<223> OTHER INFORMATION: synthetic olygonucleotide, primer for AHAY

<400> SEQUENCE: 59
gcgcacgcgt acttggcgtc cgtcattcca gat            33

<210> SEQ ID NO 60
<211> LENGTH: 33
<212> TYPE: DNA
<213> ORGANISM: Artificial
<220> FEATURE:
<223> OTHER INFORMATION: synthetic olygonucleotide, primer for AHAL

<400> SEQUENCE: 60
caacgcgtgc gcgcccttga cttctttggt cag            33

<210> SEQ ID NO 61
<211> LENGTH: 33
<212> TYPE: DNA
<213> ORGANISM: Artificial
<220> FEATURE:
<223> OTHER INFORMATION: synthetic olygonucleotide, primer for AHAL

<400> SEQUENCE: 61
gcgcacgcgt tgttggcgtc cgtcattcca gat            33

<210> SEQ ID NO 62
<211> LENGTH: 33
<212> TYPE: DNA
<213> ORGANISM: Artificial
<220> FEATURE:
<223> OTHER INFORMATION: synthetic olygonucleotide, primer for AAPF

<400> SEQUENCE: 62
gaagggcgcc gcgcccttga cttctttggt cag            33

<210> SEQ ID NO 63
<211> LENGTH: 33
<212> TYPE: DNA
<213> ORGANISM: Artificial
<220> FEATURE:
<223> OTHER INFORMATION: synthetic olygonucleotide, primer for AAPF

<400> SEQUENCE: 63
gcggcgccct tcttggcgtc cgtcattcca gat            33

<210> SEQ ID NO 64
<211> LENGTH: 33

-continued

```
<212> TYPE: DNA
<213> ORGANISM: Artificial
<220> FEATURE:
<223> OTHER INFORMATION: synthetic olygonucleotide, primer for AAPY

<400> SEQUENCE: 64
gtagggcgcc gcgcccttga cttctttggt cag                                33

<210> SEQ ID NO 65
<211> LENGTH: 33
<212> TYPE: DNA
<213> ORGANISM: Artificial
<220> FEATURE:
<223> OTHER INFORMATION: synthetic olygonucleotide, primer for AAPY

<400> SEQUENCE: 65
gcggcgccct acttggcgtc cgtcattcca gat                                33

<210> SEQ ID NO 66
<211> LENGTH: 33
<212> TYPE: DNA
<213> ORGANISM: Artificial
<220> FEATURE:
<223> OTHER INFORMATION: synthetic olygonucleotide, primer for AAPM

<400> SEQUENCE: 66
catgggcgcc gcgcccttga cttctttggt cag                                33

<210> SEQ ID NO 67
<211> LENGTH: 33
<212> TYPE: DNA
<213> ORGANISM: Artificial
<220> FEATURE:
<223> OTHER INFORMATION: synthetic olygonucleotide, primer for AAPM

<400> SEQUENCE: 67
gcggcgccca tgttggcgtc cgtcattcca gat                                33
```

METHOD OF PRODUCING PROTEINS

This application is a continuation under 35 U.S.C. §120 of PCT/JP2005/007518, filed Apr. 20, 2005, and claims the benefit of JP2005-005896, filed Jan. 13, 2005, and JP2004-124196, filed Apr. 20, 2004, all of which are incorporated by reference in their entireties. The Sequence Listing in electronic format filed herewith is also hereby incorporated by reference in its entirety (File Name: US-311 Seq List; File Size: 40 KB; Date Created: Oct. 19, 2006).

BACKGROUND OF THE INVENTION

1. Field of the Invention

The present invention relates to a method of secretory production (producing and secreting) of heterologous proteins in coryneform bacteria, and more particularly, to a method of secretory production of heterologous proteins, including industrially useful enzymes and physiologically active proteins, in coryneform bacteria.

2. Brief Description of the Background Art

Coryneform bacteria are extremely useful bacteria in the fermentation industry as producers of L-amino acids, such as L-glutamic acid and L-lysine, as well as nucleic acids. In addition, coryneform bacteria inherently secrete extremely low levels of proteins extracellularly as compared with molds, yeast, and *Bacillus* species bacteria. *Bacillus* are typically preferable when secreting heterologous proteins, since purification of the heterologous proteins can be simplified or abbreviated. Coryneform bacteria also grow rapidly in a simple medium containing sugars, ammonia, and inorganic salts, making them superior in terms of cost, culturing method, and culture productivity, and are considered to be extremely useful bacteria in the production of heterologous protein as well.

Examples of methods for efficiently producing and secreting heterologous proteins using coryneform bacteria include secretion of nuclease and lipase by *Corynebacterium glutamicum* (to be abbreviated as *C. glutamicum*) (U.S. Pat. No. 4,965,197, J. Bacteriol., 174, 1854-1861 (1992)), secretion of protease such as subtilisin (Appl. Environ. Microbiol., 61, 1610-1613 (1995)), secretion of cellular surface layer protein of coryneform bacteria (Japanese International Patent Application Laid-open No. H6-502548), secretion of fibronectin-bound protein using coryneform bacteria (Appl. Environ. Microbiol., 63, 4392-4400 (1997)), secretion of a protein using a mutant secretion component (Japanese Patent Application Laid-open No. H11-169182), producing and secreting transglutaminase (Appl. Environ. Microbiol., 69, 358-366 (2003)), and producing and secreting transglutaminase using a mutant strain (WO 02/81694). In terms of the amount of protein able to be produced, accumulation of about 2.5 mg/ml of protein has been observed in *C. glutamicum* when expressing an alkaline protease gene derived from *Dichelobacter nodosus* using a promoter of the subtilisin gene (aprE) derived from *Bacillus subtilis*, a ribosome binding site, and a signal peptide sequence (Appl. Environ. Micribiol., 61, 1610-1613 (1995)). Regarding the secretion of transglutaminase, a a maximum amount of 930 mg/L has been confirmed (WO 02/81694).

The previously known pathway of protein secretion in coryneform bacteria is the pathway known as the Sec system (machine). The Sec machine is present in inner cytoplasmic membranes, and is composed of components primarily containing SecY (Japanese Patent Application Laid-open No. H6-169780), SecE (Japanese Patent Application Laid-open No. H6-277073), and SecG (Japanese Patent Application, Laid-open No. H11-169182), which function as protein secretion channels, and SecA (Japanese Patent Application Laid-open No. H7-107981) which functions as the driving force for protein permeation. This system is present in a wide range of microorganisms, ranging from prokaryotes including *Escherichia coli* and *Bacillus subtilis*, to eukaryotes including yeasts, molds, and humans, and is the most important and most common protein secretion pathway.

However, it is difficult to secrete some proteins using the Sec system in coryneform bacteria, and examples of such proteins include industrially useful proteins such as isomaltodextranase and protein transglutaminase.

A protein secretion pathway which is completely different from the Sec system was recently discovered in the thylakoid membrane of plant cell chloroplasts (EMBO J., 14, 2715-2722 (1995)). An arginine-arginine sequence is common to the signal sequences of proteins secreted through this pathway (EMBO J., 14, 2715-2722 (1995)), and as a result, this pathway has come to be referred to as the Tat system (Twin-Arginine Translocation system). Subsequently, this Tat system was determined to be specifically involved in the secretion of proteins having the common arginine-arginine signal sequence such as *E. coli* reductokinase, nitrate reductase, *Bacillus subtilis* lipoic acid synthetase, and phosphodiesterase (Science, 278, 1467-1470 (1997), U.S. Pat. Nos. 6,022,952, 6,335,178, J. Biol. Chem., 275, 41350-41357, International Patent Publication No. WO 02/22667).

In addition, while a protein is secreted before folding in the Sec system, the Tat system is characteristic in that a folded protein is secreted through the cell membrane (J. Biol. Chem., 25, 273(52), 34868-74 (1998)).

Although genes which have high homology with the genes encoding the Tat system components are present in coryneform bacteria as well, including tatA (GENEBANK cg103060 1571065-1571382), tatB (GENEBANK cg103060 1167110-1167580), tatC (GENEBANK cg103060 1569929-1570873), and tatE (gi|41223046|emb|CAF18991.1|), their functions are not known, and it is not known whether proteins are secreted by the Tat system pathway in coryneform bacteria.

In addition, although there are reports of improved secretion into the periplasm using the Tat pathway when introducing a plasmid which expresses the tatA, tatB, and tatC genes into *E. coli*, only about 5 to 10 mg/L cells was produced, which is not an industrially practical level (Biochem. Biophys. Res. Commun., 304, 279-284 (2003)).

SUMMARY OF THE INVENTION

An object of the present invention is to provide a method for efficiently secreting (secretory production) extracellularly in coryneform bacteria an industrially useful heterologous protein which is difficult to secrete using the Sec system, which is one of the pathways for secreting proteins.

More specifically, an object of the present invention is to provide a method for efficiently producing heterologous protein by producing and efficiently secreting (secretory production) an industrially useful heterologous protein which is difficult to secrete through the Sec system, one of the protein secretion pathways, in coryneform bacteria.

As a result of focusing on the mechanism of the protein secretion pathways in coryneform bacteria, the inventors found that the Tat system, which is a protein secretion pathway which differs from the previously known Sec system, was able to function in coryneform bacteria. More specifically, the inventors discovered a phenomenon in which previously secreted proteins are no longer secreted by causing a defect in a gene encoding a protein considered to compose the Tat system which is a protein secretion pathway in coryneform bacteria, which confirmed that the Tat system also functioned in coryneform bacteria. Moreover, the inventors discovered a Tat system-dependent signal sequence, and found that a target protein can be efficiently secreted by introducing a genetic construct into coryneform bacteria, which genetic construct contains a gene sequence of a target protein, which is difficult to secrete with the Sec system, a previously known protein secretion pathway, connected downstream to a sequence encoding the signal, and culturing the resulting transformed coryneform bacteria. The inventors also found that heterologous proteins which are difficult to secrete by the conventional protein secretion pathway of the Sec system, such as isomaltodextranase and protein-glutaminase, can be efficiently secreted by using the Tat system, a newly discovered protein secretion pathway of in coryneform bacteria, which led to the present invention. In addition, the inventors also found that amount of secretable protein can be improved using the Tat system by amplifying a gene encoding the Tat system secretion components in coryneform bacteria.

It is an object of the present invention to provide a method for producing heterologous protein, comprising culturing coryneform bacteria harboring an expression construct comprising a promoter which functions in coryneform bacteria, a nucleic acid sequence which encodes a Tat system-dependent signal peptide, and a nucleic acid sequence encoding a heterologous protein in the direction from 5'-end to 3'-end, and producing and secreting the heterologous protein.

It is a further object of the present invention to provide the above-specified method for producing heterologous protein, wherein the signal peptide is selected from a group consisting of the sequence shown in SEQ ID NO. 31 and 32.

It is a further object of the present invention to provide the above-specified method for producing heterologous protein, wherein the signal peptide is selected from the group consisting of the sequence shown in SEQ ID NO. 28, 29, and 30.

It is a further object of the present invention to provide the above-specified method for producing heterologous protein, wherein the signal peptide is the signal peptide of isomaltodextranase or the signal peptide of trimethylamine-N-oxide reductase.

It is a further object of the present invention to provide the above-mentioned method for producing heterologous protein, wherein the signal peptide of isomaltodextranase comprises an amino acid sequence described in SEQ ID NO. 6, or the signal peptide of trimethylamine-N-oxide reductase comprises the amino acid sequence described in SEQ ID NO. 8.

DESCRIPTION OF THE PREFERRED EMBODIMENTS

In the method of the present invention, coryneform bacteria are used as a host-vector. An expression construct is produced in which the gene of a target protein is connected downstream from a Tat system-dependent signal peptide of coryneform bacteria. This expression construct is inserted into the coryneform bacteria and expressed so that the target protein is secreted extracellularly.

As used in the specification, "secretion" of a protein or peptide means that a molecule of the protein or peptide is transported to the outside of the bacterial cell (extracellularly), and includes when the protein or peptide molecule is ultimately placed in a completely free form in the medium, when only a portion of the protein is present outside of the bacteria, and when the protein is present on the surface layer of the bacteria.

Secretory proteins are typically translated as prepeptides or prepropeptides, after which they become mature proteins. Namely, it is known that after being translated as a prepeptide or prepropeptide, a signal peptide (pre-region) is typically cleaved to produce a mature peptide or propeptide, and a pro-region of the propeptide is known to be further cleaved by a protease resulting in the mature peptide. In addition, as used in the specification a "signal sequence" refers to a sequence present on the N-terminal side of a secretory protein precursor but absent in the naturally-occurring mature protein, and a "signal peptide" refers to a peptide cleaved from such a protein precursor. In general, a signal sequence is cleaved by a protease (typically referred to as a signal peptidase) when secreted extracellularly. Although such signal peptides have constant, common features in their sequences among biological species, a signal peptide which exhibits a secretory function in a certain biological species does not necessarily exhibit a secretory function in another biological species.

In the present invention, a protein having both a signal peptide and a pro-region, namely a primary translation product, may be referred to as a "preproprotein", while a protein having a pro-region but not a signal peptide may be referred to as a "proprotein". The pro-region of a protein may be referred to as a "pro-structural portion" or simply a "pro-structure", and as used in the specification, a "pro-structural portion/pro-structure" of a protein and a "pro-region" of a protein are used interchangeably. In a preproprotein or preprotein, the signal peptide may be a signal peptide which naturally occurs in the target protein or it may be a signal peptide for a different protein, it is preferably derived from the secretory protein of the chosen host. Alternatively, it may also be modified so as to have the optimum codon corresponding to codon usage in the chosen host. Moreover, the signal peptide of the present invention may contain the N-terminal portion of a naturally-occurring mature protein from which the signal peptide is derived. When the signal peptide is derived from a different protein, the preprotein may be referred to as a "heterologous fusion preproprotein".

For example, when the protein is a protein-glutaminase, it is respectively referred to as "preproprotein-glutaminase", "proprotein-glutaminase", and "heterologous fusion preprotein-glutaminase". In addition, a protein in which the "pro portion has been cleaved" includes a protein from which at least one amino acid from the pro-region has been removed by cleavage of the peptide bond, and also includes a protein in which the N-terminal region thereof completely corresponds to that of the naturally-occurring mature protein, and as long as the activity of the protein is retained, it also contains a protein having one more excess amino acids derived from a pro portion on the N-terminal as compared with the naturally-occurring protein, as well as a protein in which the amino acid sequence is shorter than the naturally-occurring protein.

In the present invention, the "Tat system" is a pathway which can also be referred to as the "twin-arginine-translocation pathway". This refers to a mechanism or pathway which recognizes the arginine-arginine conserved in a signal peptide, and by which a protein is secreted by a membrane protein, including TatA, B, C, and E. In addition, a "Tat system secretion component" refers to membrane proteins TatA, B, C, and E. The TatA, B, C, and E are transmembrane proteins located in the cell membrane. They are thought to form a complex which forms a pore through which a protein can be transported across the cell membrane. In addition, further research is currently in progress on the structures and functions of TatA, B, C, and E during protein transport. The gene encoding TatA and the gene encoding TatC are located in extremely close proximity in *C. glutamicum* ATCC13869.

The gene sequence encoding TatA and the 5'-upstream region thereof, along with the gene sequence encoding TatC, are shown in SEQ ID NO. 38. In addition, the amino acid sequence of TatA is shown in SEQ ID NO. 46, while the amino acid sequence of TatC is shown in SEQ ID NO. 10. The gene sequence encoding TatB and the 5'-upstream region thereof are shown in SEQ ID NO. 41, the amino acid sequence of TatB is shown in SEQ ID NO. 47, the gene sequence encoding TatE is shown in SEQ ID NO. 48, and the amino acid sequence of TatE is shown in SEQ ID NO. 49. TatA and TatE share an extremely high degree of homology, and in *E. coli*, the functions of TatA and TatE are known to be complementary (EMBO J., 1:17(13): 3640-3650 (1998)).

In the coryneform bacteria used in the present invention, the Tat system secretion components which may be amplified are not limited to the Tat system secretion components in *C. glutamicum*, but may include any Tat system secretion components which are able to function in coryneform bacteria, including the case in which a region of the amino acid sequence of the component has been deleted or added.

A secretion signal according to this system has a "Tat system-dependent signal peptide" (also referred to as a "Twin-arginine signal peptide"). The "Tat system-dependent signal peptide" refers to a signal peptide which is recognized by the Tat system and which contains the arginine-arginine consensus motif. Examples of "Tat dependent signal peptides" include signal peptides of trimethylamine-N-oxidoreductase (TorA) of *E. coli*, SufI (suppressor of ftsI: ftsI suppressor) of *E. coli*, PhoD (phosphodiesterase) of *Bacillus subtilis*, LipA, and isomaltodextranase (IMD) derived from *Arthrobacter globiformis*. The amino acid sequences of these signal peptides are indicated below:

```
TorA signal peptide:
                                            (SEQ ID NO. 8)
MNNNDLFQASRRRFLAQLGGLTVAGMLGPSLLTPRRATA SufI signal peptide:
                                            (SEQ ID NO. 28)
MSLSRRQFIQASGIALCAGAVPLKASA PhoD signal peptide:
                                            (SEQ ID NO. 29)
MAYDSRFDEWVQKLKEESFQNNTFDRRKFIQGAGKIAGL SLGLTIAQS LipA signal peptide:
                                            (SEQ ID NO. 30)
MKFVKRRTTALVTTLMLSVTSLFALQPSAKAAEH IMD signal peptide:
                                            (SEQ ID NO. 6)
MMNLSRRTLLTTGSAATLAYALGMAGSAQA
```

Furthermore, the TorA signal peptide, SufI signal peptide, PhoD signal peptide, LipA signal peptide, or IMD signal peptide, in addition to the peptides having the above-mentioned SEQ ID NO. 8, 28, 29, 30 or 6, respectively, also include peptides which have a substitution, deletion, insertion, or addition of one or several amino acids in each sequence. The term "several" normally refers to 1 to 7, preferably 1 to 5, and particularly preferably 1 to 2 amino acids, although it depends on the locations and types of amino acid residues in these Tat system-dependent signal peptides. In addition, the signal peptide may be 85% or more, preferably 90% or more, more preferably 95% or more homologous with the amino acid sequences shown in SEQ ID NO. 8, 28, 29, 30 or 6.

A nucleic acid sequence encoding a signal peptide which has such substitutions, deletions, insertions, or additions can be obtained from variants, naturally occurring mutants, or artificial mutants of *E. coli, Bacillus subtilis, Arthrobacter globiformis, Arthrobacter* species other than *Arthrobacter globiformis*, and *Bacillus* species other than *Bacillus subtilis*. In addition, nucleic acid sequences encoding Tat system-dependent signal peptides having a substitution, deletion, addition or insertion can be obtained by in vitro mutagenesis or site-specific mutagenesis of a nucleic acid encoding the Tat system-dependent signal peptide having an amino acid sequence shown in one of SEQ ID NO. 8, 28, 29, 30 or 6. Such mutagenesis can be carried out by those skilled in the art using commonly known methods.

The above-mentioned substitutions, deletions, insertions, or additions are conservative mutations, such that a consensus motif, which will be described hereinafter, is retained. A conservative mutation is typically a conservative substitution. Examples of conservative substitutions include substitution of Ala with Ser or Thr, substitution of Arg with Gln, His or Lys, substitution of Asn with Glu, Gln, Lys, His, or Asp, substitution of Asp with Asn, Glu, or Gln, substitution of Cys with Ser or Ala, substitution of Gln with Asn, Glu, Lys, His, Asp, or Arg, substitution of Glu with Asn, Gln, Lys or Asp, substitution of Gly with Pro, substitution of His with Asn, Lys, Gln, Arg or Tyr, substitution of Ile with Leu, Met, Val or Phe, substitution of Leu with Ile, Met, Val or Phe, substitution of Lys with Asn, Glu, Gln, His or Arg, substitution of Met with Ile, Leu, Val or Phe, substitution of Phe with Trp, Tyr, Met, Ile or Leu, substitution of Ser with Thr or Ala, substitution of Thr with Ser or Ala, substitution of Trp with Phe or Tyr, substitution of Tyr with His, Phe or Trp, and substitution of Val with Met, Ile or Leu.

In the "Tat system-dependent signal peptide", a hydrophobic region with the consensus motif of S/T-R-R-X-F-L-K (SEQ ID NO. 31) or R-R-X-#-# (#: hydrophobic residue) (SEQ ID NO. 32) is conserved. However, even though these consensus motifs are preserved, they are also affected by the proteins to be secreted. For example, although signal peptides WprA and WapA of *Bacillus subtilis* have the Twin-arginine motif, it has been demonstrated that they are secreted by the SRP/Sec system rather than the Tat system (Biochem Biophys Res Commun. 2003 Apr 25: 304(1): 48-54). Examples of proteins which can be secreted by the Tat system include, but are not limited to, TorA and SufI derived from *E. coli*, PhoD derived from *Bacillus subtilis*, and LipA derived from *Bacillus subtilis*. In coryneform bacteria in particular, examples of proteins which can be secreted using the Tat system include various enzymes such as an isomaltodextranase, a protein-glutaminase and a transglutaminase. Specific examples include, but are not limited to, the isomaltodextranase derived from *Arthrobacter globiformis* T6 (NRRL B-4425, IMA12103), preferably the isomaltodextranase having the amino acid sequence described in SEQ ID NO. 2, the protein glutaminase of *Chryseobacterium proteolyticum*, and preferably the protein-glutaminase having the amino acid sequence shown in SEQ ID NO. 4, GFP (green fluorescent protein), and the transglutaminase of *Streptoverticillium mobaraense* shown in WO 02/81694. *Arthrobacter globiformis* strain T6 is deposited as registration no. NRRL B-4425 with the Northern Utilization Research and Development Division. *Chryseobacterium roteollyticum* has been deposited in the National Institute of Bioscience and Human Technology, Agency of Industrial Technology (currently the International Patent Organism Depository, National Institute of Advanced Industrial Science and Technology, Tsukuba Central 6, 1-1-1 Higashi, Tsukuba, Ibaraki, Japan 305-8566) on Nov. 8, 2000 as FERM BP-3523.

Isomaltodextranase is an enzyme which efficiently produces isomaltose from dextran or the like. Isomaltodextranase is an industrially useful enzyme in that isomaltose can be obtained by allowing this enzyme to act on dextran or the like. Isomaltose is industrially useful as it has anticaries effects, (see Japanese Patent Application Laid-open No. 58-76063), and proliferative effects on Bifidobacterium which are useful intestinal bacteria in humans (see Japanese Patent Application Laid-open No. 61-22777). Protein-glutaminase is an enzyme which functions as a glutaminase, and is extremely useful as it acts directly on glutamine residues present in a protein without reducing the molecular weight of the protein. It also is able to deamidize without cleaving peptide bonds or causing protein crosslinking (Japanese Patent Application Laid-open No. 2001-218590). GFP refers to green fluorescent protein derived from jellyfish, and when inserted into cells by fusing to other proteins, is able to produce fluorescence at arbitrary locations within cells, thereby demonstrating effectiveness in fluorescent labeling of specific structures in vivo, causing it to be used in numerous research. These enzymes are not secreted by conventional Sec systems but are only able to be secreted by the Tat system. However, the proteins of the present invention are not limited to these enzymes, but may be any protein which is able to be secreted by coryneform bacteria using the Tat system.

The coryneform bacteria referred to in the present invention are aerobic, gram-positive bacilli, which although conventionally classified as *Brevibacterium* species, currently include bacteria consolidated into the *Corynebacterium* genus (Int. J. Syst. Bacteriol., 41, 255 (1981)), or *Brevibacterium* species bacteria extremely similar to *Corynebacterium* species. The advantages of using coryneform bacteria include the fact that they inherently secrete extremely small amounts of extracellular protein as compared with molds, yeasts, and *Bacillus* species bacteria which have been considered to be suitable for secreting heterologous proteins, thus making it possible to simplify or abbreviate the purification process during secretory production of a heterologous protein. In addition, since coryneform bacteria can be easily grown in a simple medium containing sugars, ammonia, or inorganic salts, they are also superior in terms of media costs, subculturing, and culture productivity. The examples of the coryneform bacteria include the following.

*Corynebacterium acetoacidophylum,*
*Corynebacterium acetoglutamicum,*
*Corynebacterium alkanolyticum,*
*Corynebacterium callunae,*
*Corynebacterium glutamicum,*
*Corynebacterium lilium,*
*Corynebacterium mellassecola,*
*Corynebacterium thermoaminogenes,*
*Corynebacterium herculis,*
*Brevibacterium divaricatum,*
*Brevibacterium flavum,*
*Brevibacterium immariophilum,*
*Brevibacterium lactofermentum,*
*Brevibacterium roseum,*
*Brevibacterium saccharolyticum,*
*Brevibacterium thiogenitalis,*
*Corynebacterium ammoniagenes,*
*Brevibacterium album,*
*Brevibacterium cerinum,* and
*Microbacterium ammoniaphilum.*

Specific examples include the bacterial strains listed below.

*Corynebacterium acetoacidophylum* ATCC13870,
*Corynebacterium acetoglutamicum* ATCC15806,
*Corynebacterium alkanolyticum* ATCC21511,
*Corynebacterium callunae* ATCC15991,
*Corynebacterium glutamicum* ATCC13020, ATCC13032, ATCC13060,
*Corynebacterium lilium* ATCC15990,
*Corynebacterium mellassecola* ATCC17965,
*Corynebacterium efficiens* AJ12340 (FERM BP-1539),
*Corynebacterium herculis* ATCC13868,
*Brevibacterium divaricatum* ATCC14020,
*Brevibacterium flavum* ATCC13826, ATCC14067, AJ12418 (FERM BP-2205),
*Brevibacterium immariophilum* ATCC14068,
*Brevibacterium lactofermentum* ATCC13869,
*Brevibacterium roseum* ATCC13825,
*Brevibacterium saccharolyticum* ATCC14066,
*Brevibacterium thiogenitalis* ATCC19240,
*Corynebacterium ammoniagenes* ATCC6871, ATCC6872,
*Brevibacterium album* ATCC15111,
*Brevibacterium cerinum* ATCC15112, and
*Microbacterium ammoniaphilum* ATCC15354.

These organisms can be obtained from, for example, the American Type Culture Collection. Namely, a deposit number has been assigned for each microbial strain, and these deposit numbers are listed in the catalog of the American Type Culture Collection, which allows each microbial strain to be ordered by referring to these numbers.

In particular, *C. glutamicum* AJ12036 (FERM BP-734) (originally deposited on March 26, 1984) (currently deposited at the International Patent Organism Depositary, National Institute of Advanced Industrial Science and Technology, Tsukuba Central 6, 1-1-1 Higashi, Tsukuba, Ibaraki, Japan 305-8566), was isolated as a streptomycin (Sm)-resistant mutant strain from wild-type strain *C. glutamicum* ATCC13869. This strain is expected to contain a mutation in a functional gene involved in protein secretion, and demonstrates extremely high heterologous protein production and secretion ability which is 2 to 3 times greater than that of the parent strain (wild strain) when determined under optimum culturing conditions, therefore making it suitable as a host organism (see WO 02/081694).

Moreover, it is particularly preferable to use a modified microbial strain as a host which does not produce cell surface layer proteins, as the purification of heterologous protein secreted into a medium is easier. Such a modification can be carried out by introducing a mutation into the cell surface layer protein or into the expression regulatory region thereof located on the chromosome using a mutagenesis or gene recombination method. An example of a coryneform bacteria which has been modified not to produce cell surface layer protein is *C. glutamicum* strain YDK010, a cell surface layer protein (PS2)-disrupted strain derived from AJ12036 (International Publication WO 02/081649).

A genetic construct used in the present invention typically contains a promoter, a sequence encoding a suitable signal peptide, a nucleic acid fragment encoding a target protein, and a control sequence (such as an operator or terminator) which is required to express the target protein gene in coryneform bacteria, all of which are placed at suitable locations so that they are able to function. The target protein may have a pro-structure at the N-terminal end. There are no particular limitations on the vector used for this construct, and may be a vector which self-replicates extrachromosomally such as a plasmid, or a vector which is incorporated into the bacterial chromosome, so long as it can function within the coryneform bacteria. Examples of these vectors include PAM330 (Japanese Patent Application Laid-open No. 58-067699), pHM1519 (Japanese Patent Application Laid-open No. 58-77895), and pSFK6 (Japanese Patent Application Laid-open No. 2000-262288). In addition, when a DNA fragment which confers the ability to self-replicate in coryneform bacteria to a plasmid is excised from these vectors and inserted into the above-mentioned *E. coli* vector, the vector can be used as a so-called shuttle vector capable of replicating in both *E. coli* and coryneform bacteria. In addition, an artificial transposon and so on can also be used. In the case of using a transposon, a target gene will be introduced into a chromosome by homologous recombination or by a transposable ability thereof.

There are no particular limitations on the promoter which can be used in the present invention, and any promoter can be used provided that it can function in coryneform bacterial cells, and may also be a heterologous promoter such as a tac promoter or another promoter from *E. coli*. Potent promoters such as the tac promoter are more preferable. Examples of coryneform bacteria-derived promoters include the gene promoters of cell surface layer proteins PS1, PS2, and SlpA, and each of the promoters of various amino acid biosynthesis genes such as glutamate dehydrogenase gene involved in glutamic acid biosynthesis, glutamine synthetase gene involved in glutamine biosynthesis, aspartokinase gene involved in lysine biosynthesis, homoserine dehydrogenase gene involved in threonine biosynthesis, acetohydroxy acid synthetase gene involved in isoleucine and valine biosynthesis, 2-isopropyl malic acid synthetase gene involved in leucine biosynthesis, glutamate kinase gene involved in proline and arginine biosynthesis, phosphoribosyl-ATP pyrophosphorylase gene involved in histidine biosynthesis, deoxyarabinoheptulonate (DAHP) gene involved in the biosynthesis of aromatic amino acids such as tryptophan, tyrosine and phenylalanine, and phosphoribosyl pyrophosphate (PRPP) amidotransferase gene, inosinate dehydrogenase gene and guanylate synthetase gene involved in nucleic acid biosynthesis such as inosinic acid and guanylic acid biosynthesis.

There are no particular limitations on the signal peptide used in the present invention provided it is a Tat system-dependent signal peptide which can function within coryneform bacterial cells. Any Tat system-dependent signal peptide which can function within coryneform bacterial cells can be used. Thus, a Tat system-dependent signal peptide of heterologous origin such as the peptide derived from *E. coli* or *Bacillus subtilis* can be used in the present invention provided that it can function within coryneform bacterial cells. A signal peptide may contain a portion of the N-terminal amino acid sequence of the secretory protein from which the signal peptide is derived. The signal sequence is cleaved by a signal peptidase when the translated product is secreted by the bacterial cells. Furthermore, although a naturally occurring signal peptide gene can be used, modified genes may also be used so as to have optimal codons depending on the codon usage of the chosen host. When using these signal peptides, a gene encoding a target protein will be located such that the gene is connected toward the 3'-terminal of a gene encoding the signal peptide, or downstream of the signal peptide gene, and the expression is controlled by the above-mentioned promoter.

Useful proteins which can be produced and secreted according to the present invention include any protein, regardless of whether inherently secreted with the Tat system or secreted with the Sec system, including intracellular proteins derived from plants and microorganisms, provided that they are proteins encoded by a nucleic acid which can be included in the same genetic construct as a nucleic acid sequence encoding the above-mentioned Tat system-dependent signal peptide. Examples of proteins which can be secreted and produced according to the present invention include proteases, aminopeptidases, carboxypeptidases, collagenases, and chitinases. Particularly, proteins which are not able to be secreted by the conventional Sec system are suitable for being produced and secreted according to the present invention. Genes encoding these proteins can be modified depending on the host used and/or to obtain a desired activity. The modification includes one or more amino acid additions, deletions or substitutions and so on. Conversion to optimal codons may be performed depending on the codon usage of the host, if necessary. These typical molecular biology techniques, including modification technology, gene cloning technology, and produced protein detection technology, are well known among those skilled in the art, and one can refer to, for example, Sambrook et al., 1989, Molecular Cloning: A Laboratory Manual, Second Edition (1989) Cold Spring Harbor Laboratory Press, Cold Spring Harbor, New York; DNA Cloning: A Practical Approach, Volumes I and II (D. N. Glover ed. 1985); F. M. Ausubel et al. (eds), Current Protocols in Molecular Biology, John Wiley & Sons, Inc. (1994); PCR Technology: Principles and Application for DNA Amplification, H. Erlich, ed., Stockton Press.

There are no particular limitations on the method for introducing a genetic construct which can be used in the present invention into coryneform bacteria, and conventionally used methods can be employed, for example, the protoplast method (Gene, 39, 281-286 (1985)) and electroporation (Bio/Technology, 7, 1067-1070 (1989)).

In addition, in the present invention, the coryneform bacterium may be a strain in which the tat system secretion components have been amplified, namely a strain in which membrane proteins including TatA, B, C and E, have been amplified. Such a coryneform bacterium is obtained by enhancing the expression of one or more of the genes containing tatA, tatB, tatC, and tatE, encoding tat system secretion component of the parent strain.

Enhancing the expression of the genes encoding the tat system secretion components, including tatA, tatB, tatC, and tatE (each of which is referred to as a "tat gene"), is achieved by increasing the copy number of one or more of the tat genes. For example, a fragment encoding a gene containing tatA, or a fragment encoding a gene containing tatA and tatB, may be connected to a vector which functions in coryneform bacteria, preferably a multicopy vector, to produce recombinant DNA, which in turn is introduced and transformed into coryneform bacteria as described above. Vectors used at this time are the same as the vectors which can be used for the above-mentioned gene construct. In addition, increasing the copy number is achieved by transferring one or more copies of the genes encoding the tat system secretion components to a chromosome. Insertion of one or more copies of the tat genes into chromosomal DNA of coryneform bacteria is carried out by homologous recombination using, as a target, a multi-copy sequence existing on the chromosomal DNA. As a multi-copy sequence present in the chromosomal DNA, a repetitive DNA or an inverted repeat present at the terminal of a transposable factor can be used. Alternatively, as is disclosed in Japanese Patent Application Laid-open No. 2-109985, multiple copies can also be inserted into a chromosomal DNA by loading a tat gene onto a transposon and transferring the transposon (Japanese Patent Application Laid-open No. 2-109985; Japanese Patent Application Laid-open No. 7-107976; Vertes, A. A., Asai, Y., Inui, M., Kobayashi, M., Kurusu, Y. and Yukawa, H.: Mol. Gen. Genet., 245, 397-405 (1994)). Introduction of the tat gene onto a chromosome may be verified by carrying out Southern hybridization using a portion of the tat gene as a probe.

In addition to gene amplification as described above, increased expression of the tat system secretion component is also achieved by substituting an expression regulatory sequence, such as the promoter of the tat gene, locating on the chromosomal DNA or on a plasmid with a more powerful expression regulatory sequence, or by modifying a factor such as an operator or repressor involved in the regulation of the expression of the tat gene (Hamilton et al.: Journal of Bacteriology 171:4617-4622). Known examples of strong promoters include lac promoter, trp promoter, and trc promoter. Methods for evaluating promoter strength and examples of strong promoters are described in, for example, Goldstein et al. (Prokaryotic promoters in biotechnology. Biotechnol. Annu. Rev., 1995, 1, 105-128). In addition, as is disclosed in International Publication WO 00/18935, a promoter can be modified to be a stronger promoter by inserting or substituting several nucleotides into the promoter region of a target gene. Moreover, substitution in a spacer region between a ribosome binding site (RBS) and initiation codon, particularly substitution of several nucleotides in the sequence located immediately upstream from the initiation codon, is known to exhibit an extremely large effect on mRNA translation efficiency, and therefore these spacer and nucleotides can also be modified. The promoter or other expression regulatory sequence of tat gene can be determined using a promoter detecting vector or genetic analysis software such as GENETYX. Substitution of the expression regulatory sequence can be carried out, for example, in the same manner as the gene substitution using the above-mentioned temperature-sensitive plasmid.

The resulting gene-introduced transformant can be cultured in accordance with ordinarily used methods and conditions. For example, the transformant can be cultured in ordinary media containing carbon sources, nitrogen sources and inorganic ions. Moreover, in order to obtain high growth, organic trace nutrients such as vitamins and amino acids can also be added, if necessary. Examples of the carbon sources which can be used include carbohydrates like glucose and sucrose, organic acids like acetic acid, alcohols and other carbon sources. Examples of the nitrogen sources which can be used include ammonia gas, ammonia water, ammonium salts and other nitrogen sources. Examples of the inorganic ions which can be suitably used include calcium ion, magnesium ion, phosphate ion, potassium ion and iron ion, if necessary. The culture may be carried out under aerobic conditions within a suitable range of pH 5.0 to 8.5 and at a temperature of 15 to 37° C., for about 1 to 7 days. As a result of culturing the transformant under such conditions, the target protein is produced in a large amount in the cells, and is efficiently secreted extracellularly.

The protein secreted into a medium according to the present invention can be isolated and purified from the medium after culturing in accordance with methods well known to those skilled in the art. For example, after removing bacterial cells by centrifugal separation and so on, the protein can be isolated and purified by a suitable known method such as salting out, ethanol precipitation, ultrafiltration, gel filtration chromatography, ion exchange column chromatography, affinity chromatography, fast protein liquid chromatography, reverse phase chromatography or hydrophobic chromatography, or a combination thereof. The protein secreted into a cell surface layer according to the present invention can also be isolated and purified in the same manner as when secreted into a medium after solubilizing the protein by a method well known to those skilled in the art, such as increasing the salt concentration or using a surfactant. In addition, in certain cases the protein secreted into a cell surface layer may also be used without being solubilized, for example, as an immobilized enzyme.

Although the following provides a more detailed explanation of the present invention using the following examples, the present invention should not be understood to be limited by these examples in any sense.

EXAMPLE 1

Secretory Expression of Isomaltodextranase Using a Signal Sequence of Isomaltodextranase Derived from Arthrobacter globiformis (1-1) Construction of a Plasmid for Secretory Expression of Isomaltodextranase Using a Signal Sequence of Isomaltodextranase by *C. glutamicum*

The sequence of the *Arthrobacter globiformis* strain T6-derived isomaltodextranase gene (EC.3.2.1.94; 1,6-α-D-glucan isomalto-dextranase) has previously been determined (Journal of Bacteriology, 176, 7730-7734 (1994)). Referring to this sequence, primers were synthesized having the sequences shown in SEQ ID NO. 11 (5'-ATGATGAACCT-GTCCCGCCG-3') and SEQ ID NO. 12 (5'-CGCGGATC-CCTGAGGGCGGGAAC-3'), and a region encoding isomaltodextranase was amplified by PCR using chromosomal DNA of *Arthrobacter globiformis* as a template prepared in accordance with an ordinary method (Saitoh and Miura (Biochim. Biophys. Acta, 72, 619 (1963)). Pyrobest DNA Polymerase (Takara) was used for the PCR reaction, and the reaction conditions were in accordance with the manufacturer's recommended protocol. The sequence of SEQ ID NO. 12 contained a BamHI restriction enzyme recognition sequence.

In addition, a region encoding a promoter and signal sequence was amplified using the above-mentioned pPK-SPTG1 (WO 01/23591) as a template by PCR using the primers shown in SEQ ID NO. 14 (5'-AAATTCCTGT-GAATTAGCTGATTTAG-3') and SEQ ID NO. 16 (5'-GGCGGGACAGGTTCATCATAGAGGC-GAAGGCTCCTTGAA-3'). The sequence shown in SEQ ID NO. 16 contained a region encoding the N-terminal region of the signal sequence of isomaltodextranase.

The PCR product which had been amplified with primers having the sequences shown in SEQ ID NO. 11 and SEQ ID NO. 12, and the PCR product which had been amplified with the primers shown in SEQ ID NO. 14 and SEQ ID NO. 16 were admixed, and these were used as templates in crossover PCR using the primers shown in SEQ ID NO. 12 and SEQ ID NO. 14. After digesting this PCR product with restriction enzymes ScaI and BamHI, an about 2.5 kb DNA fragment was recovered through agarose gel electrophoresis, and this fragment was inserted into the ScaI-BamHI region of pPK-SPTG1 (described in WO 01/23591) to construct isomaltodextranase expression plasmid pPKI-IMD. The sequence of the gene inserted into the constructed plasmid was determined using the DyeTerminator Cycle Sequencing Kit (PE Applied Biosystems) and the DNA Sequencer 377A (PE Applied Biosystems). As a result of determining the nucleotide sequence, the resulting isomaltodextranase gene was shown to differ in part from the reported sequence. The sequence of the newly determined isomaltodextranase gene is shown in SEQ ID NO. 1, while the amino acid sequence is shown in SEQ ID NO. 2.

(1-2) Secretion of IMD by *C. glutamicum* using IMD Signal Sequence

*C. glutamicum* strain YDK010 (WO 02/081649), which is a cell surface layer protein (PS2)-disrupted strain of streptomycin (Sm)-resistant strain AJ12036 which itself is derived from *C. glutamicum* ATCC13869, was transformed with the constructed plasmid pPKI-IMD, and a microbial strain which grew on CM2G agar medium containing 25 mg/l of kanamycin was selected. The selected strain was cultured for 48 hours at 30° C. in MM liquid medium containing 25 mg/l of kanamycin. After completion of culturing, 10 μl of culture supernatant was analyzed by SDS-PAGE. SDS-PAGE was carried out using 12.5% gel (Daiichi Pure Chemicals), and protein bands were detected with Coomassie Brilliant Blue staining. As a result, a band having the predicted molecular weight of about 65 kDa was detected. As a result of quantifying the protein by reverse phase chromatographic analysis, the protein concentration was determined to be about 120 mg/l. In addition, the enzyme activity of isomaltodextranase was measured according to the method described in Journal of Bacteriology, 176, 7730-7734 (1994), and the resulting protein was confirmed to have isomaltodextranase enzyme activity.

In addition, the N-terminal amino acid sequence of the secreted isomaltodextranase was analyzed with a protein sequencer. As a result, isomaltodextranase starting from the $31^{st}$ Ala of the amino acid sequence shown in SEQ ID NO. 2 was confirmed to be secreted. Thus, the signal sequence region was confirmed to be the sequence shown in SEQ ID NO. 5 (nucleotide sequence) and SEQ ID NO. 6 (amino acid sequence).

REFERENCE EXAMPLE A

Secretory Expression of Isomaltodextranase Using Signal Sequence Derived from Cell Surface Layer Protein SlpA of *Corynebacterium ammoniagenes*

(A-1) Acquisition of the Isomaltodextranase Gene from *Arthrobacter globiformis* Strain T6 (NRRL B-4425, IMA12103)

Primers having the sequences shown in SEQ ID NO. 11 and SEQ ID NO. 12 were synthesized, a region encoding isomaltodextranase was amplified by PCR from chromosomal DNA of *Arthrobacter globiformis* prepared in accordance with a conventional method (method of Saitoh and Miura (Biochim. Biophys. Acta, 72, 619 (1963)). Pyrobest DNA Polymerase (Takara) was used for the PCR reaction, and the reaction conditions were in accordance with the manufacturer's recommended protocol. Furthermore, the sequence of SEQ ID NO. 12 contained a restriction enzyme BamHI recognition sequence.

Then, using the DNA fragment amplified by the PCR as a template, PCR was carried out using the primers shown in SEQ ID NO. 13 (5'-GTCCCCGTCACGGCCGCGCC-3') and SEQ ID NO. 12 to amplify the region encoding the mature isomaltodextranase without the signal sequence.

(A-2) Construction of a Plasmid for Secretory Production of Isomaltodextranase in *C. glutamicum* Using SlpA Signal Sequence Using plasmid pPKSPTG1 described in WO 01/23591 as a template, a region encoding the promoter and signal sequence was amplified by PCR using primers having the sequences shown in SEQ ID NO. 14 and SEQ ID NO. 15 (5'-CCCGGGCGGGCGGTGACGGCGGTGGCT-GCCGTTGCC ACAGGTGCGG-3'). Plasmid pPKSPTG1, which was used for the template, contained the promoter of PS2, the cell surface layer protein derived from *C. glutamicum*, the region encoding the signal sequence derived from cell surface layer protein SlpA of *C. ammoniagenes*, and the region encoding a protransglutaminase derived from *S. mobaraense*. A fragment containing the PS2 promoter and the region encoding the SlpA signal sequence in this plasmid was amplified by the above-mentioned PCR. The primer shown in SEQ ID NO. 15 contained the sequence encoding the N-terminal side amino acid region of mature isomaltodextranase.

Then, the PCR product amplified by using the primers having the sequences shown in SEQ ID NO. 13 and SEQ ID NO. 12 in (A-1) and the PCR product amplified by using the primers having the sequences shown in SEQ ID NO. 14 and SEQ ID NO. 15 were mixed, and using them as templates, crossover PCR was carried out using primers having the sequences shown in SEQ ID NO. 14 and SEQ ID NO. 12 to amplify a fusion gene of PS2 promoter, SlpA signal peptide sequence and mature isomaltodextranase. After digesting this PCR product with restriction enzymes ScaI and BamHI, an about 2.5 kb DNA fragment was recovered by agarose gel electrophoresis and inserted into plasmid pPK4 (Japanese Patent Application Laid-open No. 9-322774) at the ScaI-BamHI site to construct an expression plasmid pPKSIMD for mature isomaltodextranase.

(A-3) Secretion of IMD Using a Signal Sequence Derived from the Cell Surface Layer Protein SlpA of *C. ammoniagenes*

*C. glutamicum* strain YDK010 (described in WO 02/081649), which is a cell surface layer protein (PS2)-disrupted strain of streptomycin (Sm)-resistant strain AJ12036 which itself is derived from *C. glutamicum* ATCC13869, was transformed with the constructed plasmid pPKSIMD, and a strain grown in CM2G agar medium containing 25 mg/l of kanamycin (yeast extract: 10 g, tryptone: 10 g, glucose: 5 g, NaCl: 5 g, agar: 15 g, brought to a volume of 1 liter with water) was selected. The selected strain was cultured for 48 hours at 30° C. in MM liquid medium containing 25 mg/l of kanamycin. Following completion of culturing, 10 μl of culture supernatant were analyzed by SDS-PAGE. SDS-PAGE was carried out using 12.5% gel (Daiichi Pure Chemicals) and protein bands were detected with Coomassie Brilliant Blue staining. As a result, an extremely weak band was detected at about 65 kDa. Moreover, as a result of quantifying the protein by reverse phase chromatographic analysis, the concentration was determined to be about 10 mg/l. This demonstrated that the amount of secreted protein had decreased as compared with when the IMD signal sequence derived from *Arthrobacter globiformis* was used. The conditions for reverse phase chromatography are indicated below.

Column: Protein C4 214TP5410 (Vydac)
Elution conditions: 24-80% acetonitrile linear gradient/ 0.1% trifluoroacetic acid
Flow rate: 1.0 m/min In addition, the enzyme activity of isomaltodextranase was measured according to the method described in Journal of Bacteriology, 176, 7730-7734 (1994), and the secreted protein was confirmed to have isomaltodextranase enzyme activity.

EXAMPLE 2

Expression and Secretion of Protein-Glutaminase which has a Pro-Structure Using the IMD Signal Sequence Derived from *Arthrobacter globiformis*

(2-1) Acquisition of Protein Glutaminase Gene from *Chryseobacterium proteolyticum*

The sequence of *Chryseobacterium proteolyticum*-derived protein-glutaminase gene (EC.3.5.1) has previously been determined (Eur. J. Biochem. 268. 1410-1421 (2001)). Referring to this sequence, the gene sequence shown in SEQ ID NO. 3 was constructed by converting codons to those highly used in *C. glutamicum*. This sequence contained a region encoding the signal sequence (pre-region) of protein-glutaminase, the pro-region and mature protein-glutaminase. This entire gene sequence was prepared by synthesis.

Primers having the sequences shown in SEQ ID NO. 17 (5'-CAT GAAGAACCTTTTCCTGTC-3') and SEQ ID NO. 18 (5'-GTAAAAGGATCCATTAATT AAAATCC-3') were synthesized based on the gene sequence data of the constructed SEQ ID NO. 3. The primer shown in SEQ ID NO. 17 contained the N-terminal sequence of the signal sequence of protein glutaminase, while the primer shown in SEQ ID NO. 18 contained the C-terminal of mature protein-glutaminase and a BamHI recognition sequence. Using the DNA having the sequence shown in SEQ ID NO. 3 as a template, PCR was carried out using the primers having the sequences of SEQ ID NO. 17 and SEQ ID NO. 18 to amplify a region encoding the pro-portion of protein glutaminase and mature protein-glutaminase. After inserting this PCR fragment into the SmaI site of pVC7 (Japanese Patent Application Laid-open No. H9-070291), it was introduced into competent cells of *E. coli* JM109 (Takara). A microbial strain harboring the plasmid with the cloned protein-glutaminase gene was acquired, and the plasmid was recovered. The nucleotide sequence of the fragment cloned in this plasmid was determined, and confirmed to coincide with the sequence shown in SEQ ID NO. 3.

(2-2) Construction of a Plasmid for Secretory Expression of Protein-Glutaminase Having Pro-structure Using IMD Signal Sequence Using the IMD expression plasmid pPKI-IMD described in (1-1) of Example 1, a region encoding a promoter and signal peptide was amplified by PCR using primers having the sequences shown in SEQ ID NO. 14 and SEQ ID NO. 21 (5'-CCTGGTTGCCGTTGGAATCGGCCTGGG CGGAGCCTGCC-3'). The amplified region contained the PS2 promoter and IMD signal peptide. Furthermore, the sequence shown in SEQ ID NO. 21 contained the 5' terminal sequence of a region encoding the protein-glutaminase with the pro-structure. Then, using as a template a plasmid with the cloned protein-glutaminase, a region encoding the protein-glutaminase with a pro-structure was amplified by PCR using primers having the sequences of SEQ ID NO. 20 (5'-GATTC-CAACGGCAACCAGGA-3') and SEQ ID NO. 18. Moreover, the PCR product obtained using the primers having the sequences of SEQ ID NO. 14 and 21, and the PCR product obtained using the primers having the sequences of SEQ ID NO. 20 and SEQ ID NO. 18 were admixed at a 1:1 ratio, and then, using them as templates, crossover PCR was carried out using primers having the sequences shown in SEQ ID NO. 14 and SEQ ID NO. 18 to amplify a fusion gene containing the PS2 promoter region, the IMD signal sequence, and the gene encoding the protein-glutaminase having the pro-structure. After digesting this crossover PCR product with restriction enzymes ScaI and BamHI, about 1.6 kbp DNA fragment was detected by agarose gel electrophoresis. This DNA fragment was then excised from the agarose gel and recovered using EasyTrap Ver. 2 (Takara), and an expression plasmid, pPKI-PPG, for protein-glutaminase having a pro-structure was constructed by inserting the fragment into ScaI-BamHI site of plasmid pPK4 (Japanese Patent Application Laid-open No. 9-322774). As a result of determining the nucleotide sequence of the gene sequence inserted in the constructed plasmid, the presence of the predicted fusion gene was confirmed.

(2-3) Secretion of Protein-Glutaminase Having a Pro-Structure by *C. glutamicum* Using IMD Signal Sequence After transforming the strain YDK010 (WO 02/081649), which was obtained from mutant strain YSr which had been in turn derived from *C. glutamicum*, with the constructed plasmid pPKI-PPG, a microbial strain grown on CM2G agar medium containing 25 mg/l of kanamycin was selected as described in (1-3) of Example 1. The selected strain was cultured for 48 hours at 30° C. in MM liquid medium containing 25 mg/l of kanamycin. Following completion of culturing, 10 µl of culture supernatant were analyzed by SDS-PAGE. SDS-PAGE was carried out using 4-20% gradient gel (Daiichi Pure Chemicals) followed by protein staining with Coomassie Brilliant Blue. As a result, a band was detected at the predicted molecular weight of about 35 kDa. As a result of analyzing 100 µl of culture supernatant by reverse phase HPLC, the protein concentration was about 20 mg/l. The conditions for reverse phase HPLC are indicated below.

Column: CAPCELL PAK C18 SG300, 4.6×150 mm (Shiseido)

Elution conditions: 32-48% acetonitrile linear gradient/ 0.1% trifluoroacetic acid (15 min)

Flow rate: 1.0 m/min

Moreover, after subjecting the culture supernatant to desalination and concentration treatment using Ultrafree (Millipore), protein was enzymatically digested with Actinomycetes-derived protease SAM-P45 (described in WO 01/23591) to cleave the pro-structure portion of protein glutaminase to obtain the mature protein. The activity of the mature protein was measured according to the method described in Japanese Patent Application Laid-open No. 2000-50887, and the secreted protein was confirmed to have protein-glutaminase activity.

REFERENCE EXAMPLE B

Secretion and Expression of Protein-Glutaminase of *Chryseobacterium proteolyticum* Using Signal Sequence Derived from Cell Surface Layer Protein SlpA of *C. ammoniagenes*

(B-1) Acquisition of Protein-Glutaminase Gene Derived from *Chryseobacterium proteolyticum*

Referring to the sequence of protein-glutaminase (EC.3.5.1) of *Chryseobacterium proteolyticum* (Eur. J. Biochem. 268, 1410-1421(2001)), the sequence shown in SEQ ID NO. 3 was generated by converting codons to those which are highly used in *C. glutamicum*. This sequence contained a region encoding the signal sequence (pre portion) of protein glutaminase, the pro-portion, and the mature protein glutaminase. A nucleic acid molecule containing this entire gene sequence was synthetically prepared.

Primers having the sequences shown in SEQ ID NO. 17 and SEQ ID NO. 18 were synthesized based on the gene sequence data of the prepared SEQ ID NO. 3. The primer having the sequence of SEQ ID NO. 17 contained the N-terminal sequence of the signal sequence of protein-glutaminase, while the primer having the sequence of SEQ ID NO. 18 contained the C-terminal of mature protein-glutaminase and a BamHI recognition sequence. Using DNA having the sequence shown in SEQ ID NO. 3 as a template, PCR was carried out using the primers having the sequences of SEQ ID NO. 17 and SEQ ID NO. 18 to amplify a region encoding the pro-portion of protein-glutaminase and the mature protein-glutaminase. After inserting this PCR fragment into the SmaI site of pVC7 (Japanese Patent Application Laid-open No. H9-070291), it was introduced into competent cells of *E. coli* JM109 (Takara). A microbial strain harboring the plasmid in which the protein-glutaminase gene was cloned was obtained, and the plasmid was recovered from the strain. The cloned nucleotide sequence of the fragment contained in this plasmid was determined, and the sequence was confirmed to coincide with the sequence shown in SEQ ID NO. 3.

(B-2) Construction of a Plasmid for Secretory Expression of Protein-Glutaminase by *C.glutamicum* Using SlpA Signal Sequence Using plasmid pPKSPTG1 described in WO 01/23591 as a template, a region encoding a promoter and signal peptide was amplified by PCR using primers having the sequences shown in SEQ ID NO. 14 and SEQ ID NO. 19 (5'-TCCTG-GTTGCCGTTGGAATCTGCCGTTGCCACAGGTGCGG-3'). The amplified region contained a region encoding the PS2 promoter and the SlpA signal peptide. The sequence shown in SEQ ID NO. 19 contained the sequence of the 5' terminal of a region encoding the protein-glutaminase having the pro-structure.

Then, using as a template the plasmid obtained in Reference Example B-1 in which the protein-glutaminase was cloned, the region encoding the protein-glutaminase gene having the pro-structure was amplified by PCR using primers having the sequences of SEQ ID NO. 20 and SEQ ID NO. 18. Moreover, the PCR product obtained using the primers having the sequences shown in SEQ ID NO. 14 and 19, and the PCR product obtained using the primers having the sequences of SEQ ID NO. 20 and SEQ ID NO. 18 were mixed in a 1:1 ratio, and then using them as templates, crossover PCR was carried out using primers having the sequences shown in SEQ ID NO. 14 and SEQ ID NO. 18 to amplify a fusion gene consisting of a sequence containing the PS2 promoter region, the SlpA signal sequence and a gene encoding the protein-glutaminase having the pro-structure. After digesting this crossover PCR product with restriction enzymes ScaI and BamHI, about 1.6 kbp DNA fragment was detected by agarose gel electrophoresis. This DNA fragment was then excised from the agarose gel and recovered using EasyTrap Ver. 2 (Takara) to construct an expression plasmid pPKS-PPG for the protein glutaminase having pro-structure by inserting the fragment into the ScaI-BamHI site of plasmid pPK4 (Japanese Patent Application Laid-open No. 9-322774). As a result of determining the nucleotide sequence of the gene sequence inserted in the constructed plasmid, the presence of the predicted fusion gene was confirmed.

(B-3) Secretion of Protein-Glutaminase Having Pro-Structure by *C. glutamicum* Using SlpA Signal Sequence After transforming the strain YDK010 (WO 02/081649) obtained from a mutant strain of *C. glutamicum* with the constructed plasmid pPKS-PPG, a microbial strain which grew on CM2G agar medium containing 25 mg/l of kanamycin was selected as described in (1-3) of Example 1. The selected strain was cultured for 48 hours at 30° C. in MM liquid medium containing 25 mg/l of kanamycin. Following completion of culturing, 10 µl of culture supernatant were analyzed by SDS-PAGE. SDS-PAGE was carried out using 12.5% gel (Daiichi Pure Chemicals) followed by protein staining with Coomassie Brilliant Blue and a fluorescent dye, SYPRO Orange (Molecular Probes). As a result, no band was detected around the location of the predicted molecular weight by either staining method.

EXAMPLE 3

Secretory Expression of Protein-Glutaminase Using TorA (Trimethylamine-N-oxidoreductase) Signal Sequence Derived from *E. coli*

(3-1) Acquisition of Gene Encoding TorA Signal Peptide Derived From *E. coli*

The sequence of the TorA gene containing the *E. coli*-derived TorA signal peptide has previously been determined (Mol. Microbiol. 11:1169-1179 (1994)). Referring to this sequence, the primers shown in SEQ ID NO. 22 (5'-ATGAA-CAATAACGATCTCTTTCAGG-3') and SEQ ID NO. 23 (5'-CCGGATCCTGGTCATGATTTCACCTG-3') were synthesized, and a region encoding TorA and a signal sequence located upstream therefrom was amplified by PCR using chromosomal DNA of *E. coli* strain W3110 prepared by ordinary methods (method of Saitoh and Miura (Biochim. Biophys. Acta, 72, 619 (1963)). Pyrobest DNA Polymerase (Takara) was used for the PCR reaction, and the reaction conditions were in accordance with the manufacturer's recommended protocol. The sequence of SEQ ID NO. 23 contains a restriction enzyme BamHI recognition sequence. The DNA sequence encoding the signal sequence of TorA is shown in SEQ ID NO. 7.

(3-2) Construction of a Plamid for Secretory Expression of Protein-Glutaminase (PPG) Having the Pro-Structure Using the TorA Signal Sequence Using plasmid pPKSPTG1 (WO01/23591 as a template, a region encoding the promoter and the signal peptide was amplified by PCR using primers having the sequences shown in SEQ ID NO. 14 and SEQ ID NO. 24 (5'-AAGAGATCGT-TATTGTTCATAGAGGCGAAGGCTCCTT GAATAG-3'). The sequence of SEQ ID NO. 24 contained the 5'-terminal sequence of the gene encoding the TorA signal peptide. Then, this PCR product was mixed in a 1:1 ratio with a PCR product containing the gene sequence which was obtained in (3-1) of Example 3 and which encoded TorA which had been amplified with primers having the sequences shown in SEQ ID NO. 22 and SEQ ID NO. 23 as well as the signal sequence upstream therefrom, and then using them as templates, crossover PCR was carried out with primers having the sequences shown in SEQ ID NO. 14 and SEQ ID NO. 23. As a result, a fusion gene was amplified containing a region containing the PS2 promoter region, the TorA signal sequence and the sequence encoding TorA. After digesting this crossover PCR product with restriction enzymes ScaI and BamHI, about 3.1 kbp DNA fragment was detected by agarose gel electrophoresis. This DNA fragment was then excised from the agarose gel and recovered using EasyTrap Ver. 2 (Takara) to obtain plasmid pPKT-TorA by inserting the fragment into ScaI-BamHI site of plasmid pPK4 described in Japanese Patent Application Laid-open No. H9-322774. As a result of determining the nucleotide sequence of the gene which had been inserted in this plasmid, the presence of the predicted fusion gene was confirmed. Then using this plasmid as a template, a segment containing the PS2 promoter region and the region encoding TorA signal peptide was amplified by PCR using primers having the sequences shown in SEQ ID NO. 14 and SEQ ID NO. 25 (5'-GATTTCCTGGTTGCCGTTGGAATCCG-CAGTCGCACGTCGCGGCG-3'). A region encoding protein-glutaminase having the pro-structure was then amplified by PCR using this PCR product and primers having the sequences shown in SEQ ID NO. 20 and SEQ ID NO. 18 in the same manner as (2-2) of Example 2. These PCR products were then mixed in a 1:1 ratio, and by using these PCR products as templates, crossover PCR was carried out using primers having the sequences shown in SEQ ID NO. 14 and SEQ ID NO. 18.

After digesting this PCR product with restriction enzymes ScaI and BamHI, about 3.1 kbp DNA fragment was detected by carrying out agarose gel electrophoresis. This DNA fragment was then excised from the agarose gel and recovered using EasyTrap Ver. 2 (Takara) to obtain plasmid pPKT-PPG by inserting the fragment into the ScaI-BamHI site of plasmid pPK4 (Japanese Patent Application Laid-open No. 9-322774). As a result of determining the nucleotide sequence of this insertion sequence in the plasmid, the presence of the predicted fusion gene was confirmed.

(3-3) Secretion of Protein-Glutaminase Having A Pro-Structure by *C. glutamicum* Using TorA Signal Sequence Strain YDK010 (described in WO 02/081649) obtained from streptomycin (Sm)-resistant strain AJ12036 derived from *C. glutamicum* ATCC13869 which is in turn a mutant strain of *C. glutamicum*, was transformed with the plasmid pPKT-PPG, and a microbial strain was selected which grew on CM2G medium containing 25 mg/l of kanamycin. The selected microbial strain was cultured for 48 hours at 30° C. in MM liquid medium containing 25 mg/l of kanamycin. Following completion of culturing, 10 μl of culture supernatant were analyzed by SDS-PAGE. SDS-PAGE was carried out using a 4-20% gradient gel (Daiichi Pure Chemicals) followed by protein staining with Coomassie Brilliant Blue. As a result, a band was detected at about 35 kDa, which is in the vicinity of the predicted molecular weight. As a result of analyzing 100 μl of culture supernatant by reverse phase HPLC, the protein concentration was determined to be about 20 mg/l.

Moreover, after treating the culture supernatant with Ultrafree (Millipore) as described in (2-2) of Example 2, the protein was enzymatically digested with Actinomycetes-derived protease SAM-P45 to cleave the pro-structure region of protein-glutaminase to obtain the mature protein. The activity of the mature protein was measured according to the method described in Japanese Patent Application Laid-open No. 2000-50887, and the secreted protein was confirmed to have protein-glutaminase activity.

The amino acid sequence of the protein-glutaminase having a pro-structure is shown in SEQ ID NO. 4.

EXAMPLE 4

Preparation of TatC-Deficient Strain (4-1) Preparation of a tatC Gene-Disrupted Strain from *C. glutamicum* AJ12036

A study was conducted to determine whether the above-mentioned isomaltodextranase connected to the IMD signal sequence, and the protein-glutaminase connected to the TorA signal sequence are respectively secreted by the Tat system. Although tatA (GENEBANK cg103060 1571065-1571382), tatB (GENEBANK cg103060 1167110-1167580), tatC (GENEBANK cg103060 1569929-1570873) and tatE (gi 41223046 emb CAF18991.1) have been clearly demonstrated to exist as homologues of the tat system genes in coryneform bacteria, their functions have yet to be identified.

Thus, it was decided to confirm whether the enzymes which were confirmed to be secreted in the above-mentioned examples are secreted by the Tat system. This was accomplished by disrupting the tat gene.

A TatC-deficient strain from strain YDK010 was obtained using homologous recombination as described below.

Using a chromosomal DNA of *C. glutamicum* ATCC13869 prepared in accordance with the method of Saitoh and Miura (Biochim. Biophys. Acta. 72, 619 (1963)) as a template, PCR was carried out using a combination of primers having the sequences shown in SEQ ID NO. 26 (5'-ggcggtaccgttaagcgc-cctcggcgagttatct-3') and SEQ ID NO. 27 (5'-gcctctagactagag-cacgtcaccgaagtcggcg-3').

This fragment was then digested with KpnI and XbaI and inserted into the KpnI-XbaI site of pHS4 (U.S. Pat. No. 5,616, 480), a temperature-sensitive plasmid vector derived from plasmid pHM1519, to construct pHStatC. *E. coli* AJ12570 transformed with plasmid pHS4 has been deposited in the National Institute of Bioscience and Human Technology, Agency of Industrial Technology on Oct. 11, 1990 as FERM BP-3523 (currently the International Patent Organism Depository, National Institute of Advanced Industrial Science and Technology, Tsukuba Central 6, 1-1-1 Higashi, Tsukuba, Ibaraki, Japan 305-8566).

Then, pHStatC was digested with NdeI and ScaI, and an internal region of the tatC gene was deleted by removing an approximately 70 bp DNA fragment, which was recircularized to generate plasmid pHSAtatC. This plasmid was inserted into YDK010 by electroporation to obtain the tatC-deficient strain, YDK011, by a homologous recombination as described in Japanese Patent No. 2763054.

(4-2) Secretion and Expression in TatC-Deficient Strain (4-2-1) Comparison of IMD Secretion Between the Strain Transformed with Isomaltodextranase (IMD) Secretory Expression Plasmid pPKS-IMD Containing SlpA-Derived Signal Sequence and the Strain Transformed with IMD Secretory Expression Plasmid pPKI-IMD Containing IMD Signal Sequence The above-mentioned TatC-deficient strain was transformed with pPKS-IMD produced in Reference Example A, an isomaltodextranase secretion and expression plasmid having a signal sequence derived from the cell surface layer protein SlpA of *C. ammoniagenes*, and a microbial strain which grew on CM2G agar medium containing 25 mg/l of kanamycin was selected to obtain strain YDK011/pPKS-IMD. In addition, TatC-deficient strain YKD011 was similarly transformed with pPKI-IMD produced in Example 1, and the IMD secretion and expression plasmid which has the IMD signal sequence to obtain strain YDK011/pPKI-IMD. Both of the obtained strains were cultured for 48 hours at 30° C. in MM medium, and the amounts of IMD secreted into the culture supernatant were compared. 10 μl of the culture supernatant of each strain were analyzed by applying to SDS-PAGE followed by protein staining using SYPRO Orange (Molecular Probes). As a result, although a very weak band was detected in the vicinity of the molecular weight of IMD for the culture supernatant of strain YDK011/pPKS-IMD, no band was detected in the vicinity of the molecular weight of IMD for the culture supernatant of strain YDK011/pPKI-IMD.

(4-2-2) Comparison of Protein-Glutaminase Secretion Between the Strain Transformed with Protein-Glutaminase Secretory Expression Plasmid pPKI-PPG Containing IMD Signal Sequence and the Strain Transformed with Protein-Glutaminase Secretory Expression Plasmid pPKT-PPG Containing the TorA Signal Sequence TatC-deficient strain YDK011 was transformed with IMD secretion and expression plasmid pPKI-PPG produced in Example 2 containing the IMD signal sequence to obtain YDK011/pPKI-PPG. Moreover, TatC-deficient strain YDK011 was transformed with protein-glutaminase (PPG) expression plasmid pPKT-PPG (Example 3) containing the TorA signal, which is the Tat system signal derived from *E. coli*, to obtain YDK011/pPKT-PPG. The thus obtained transformed strains were cultured for 48 hours at 30° C. in minimal liquid medium, and the secreted amounts of PPG in the culture supernatant were analyzed.

10 μl of each culture supernatant of strain YDK011/pPKI-PPG and strain YDK011/pPKT-PPG were applied to SDS-PAGE followed by protein staining with SYPRO Orange. As a result, PPG bands in the vicinity of a molecular weight of 35 kDa were unable to be detected in either of the culture supernatants of strain YDK011/pPKI-PPG or strain YDK011/pPKT-PPG.

Then, an anti-protein-glutaminase polyclonal antibody was produced by immunizing rabbits with protein-glutaminase. As a result of carrying out Western blotting using this polyclonal antibody, and although bands were detected in the culture supernatants of both strain YDK010/pPKI-PPG or YDK010/pPKT-PPG produced in Examples 2 and 3, PPG bands were not detected in the culture supernatants of either strain YDK011/pPKI-PGG or strain YDK011/pPKT-PPG. Moreover, the respective bacterial cells were crushed by ultrasound processing following culturing, and the protein within the cells was analyzed by SDS-PAGE. As a result of carrying out Western blotting on the protein present in the cells of each transformed strain in the same manner as carried out for the culture supernatants, PPG bands were detected in the vicinity of a molecular weight of 35 kDa for the crushed cells derived from strain YDK011/pPKI-PPG and strain YDK011/pPKT-PPG.

When using the IMD signal and TorA signal, the above result that although PPG or IMD protein is secreted into the culture supernatant of each transformed strain having normal TatC, PPG protein, or IMD protein, was not secreted into the culture supernatant of each transformed TatC-deficient strain, indicates that the IMD signal and the TorA signal is involved in the secretion of IMD or PPG by the Tat pathway.

EXAMPLE 5

Secretory Expression of Protein-Glutaminase in *C. glutamicum* ATCC13869

(5-1) Secretion of Protein-Glutaminase with a Pro-Structure in *C. glutamicum* Using TorA Signal Sequence

*C. glutamicum* ATCC13869 and YDK010 (described in WO 02/081649), obtained from the streptomycin (Sm)-resistant strain AJ12036 which is itself a mutant strain of *C. glutamicum* ATCC13869, were transformed with plasmid pPKT-PPG constructed in (3-2) of Example 3, and a bacterial strain which grew in CM2G agar medium containing 25 mg/l of kanamycin was selected as described in (1-3) of Example 1. The selected microbial strain was cultured for 48 hours at 30° C. in MM liquid medium containing 25 mg/l of kanamycin. Following completion of culturing, 10 μl of culture supernatant were analyzed by SDS-PAGE. SDS-PAGE was carried out using 4-20% gradient gel (Daiichi Pharmaceutical) followed by protein staining with Coomassie Brilliant Blue. As a result, bands were detected at the location of the predicted molecular weight of about 35 kDa in the culture supernatants of both strains. As a result of analyzing protein concentration by applying 100 μl of each culture supernatant to reverse phase HPLC, the protein concentration in the culture supernatant of *C. glutamicum* strain YDK010 harboring pPKT-PPG was about 20 mg/l, while the protein concentration in the culture supernatant of *C. glutamicum* strain ATCC13869 harboring the same pPKT-PPG was about 70 mg/l.

Moreover, after subjecting the culture supernatant to treatment using Ultrafree (Millipore) as described in (2-2) of Example 2, the protein was enzymatically digested with Actinomycetes-derived protease SAM-P45 to cleave the pro-structure region of the protein-glutaminase to obtain the mature protein. The activity of this mature protein-glutaminase was measured according to the method described in Japanese Patent Application Laid-open No. 2000-50887, and the secreted protein was confirmed to have protein glutaminase activity.

EXAMPLE 6

Effect of Amplification of Tat System Secretion Component on Secreted Amount of Protein-Glutaminase Using the TorA Signal Sequence from *E. coli*

(1) Construction of TatC Expression Plasmid

The gene encoding TatA is present upstream on the 5' region of the gene sequence encoding TatC of *C. glutamicum*. A gene sequence containing the upstream promoter region of the TatA gene was amplified by PCR. Chromosomal DNA of *C. glutamicum* ATCC13869 prepared in accordance with the method of Saitoh and Miura was used as a template, and primers having the sequences shown in SEQ ID NO. 33 (5'-GCTTGATCATTCCTTTAAGG-3') and SEQ ID NO. 34 (5'-ATGTGCTCAACAATGGACATGTGGTC-TACTCCAAATTCAC-3') were used. SEQ ID NO. 34 contains the sequence of the 5'-terminal of tatC. In addition, primers having the sequences shown in SEQ ID NO. 36 (5'-ATGTCCATTGTTGAGCACATC-3') and SEQ ID NO. 37 (5'-CTAGAGCACGTCACCGAAGT-3') were produced by referring to the gene sequence of tatC (SEQ ID NO. 35) in *C. glutamicum* ATCC13032 and the gene encoding TatC was amplified by PCR. Moreover, the PCR product which had been amplified with SEQ ID NO. 33 and SEQ ID NO. 34, and the PCR product which had been amplified using SEQ ID NO. 36 and SEQ ID NO. 37 were mixed in a 1:1 ratio and they were used as templates to carry out crossover PCR with SEQ ID NO. 33 and SEQ ID NO. 37 to amplify a fusion gene containing the tatA promoter region and the gene encoding TatC. This PCR product was subjected to agarose gel electrophoresis and an about 1.8 kb DNA fragment was recovered. TatC expression plasmid pVtatC was constructed by inserting the recovered DNA fragment into SmaI site of plasmid pVC7 described in Japanese Patent Application Laid-open No. H9-070291. The constructed plasmid was confirmed to contain the nucleotide sequence of the insertion site using a similar method as in Example 1.

(2) Construction of TatA and TatC Expression Plasmid

Using chromosomal DNA of *C. glutamicum* ATCC13869 as a template, a region containing a gene sequence encoding TatA and its 5' upstream region and a gene sequence encoding TatC was amplified by PCR using primers having the sequences shown in SEQ ID NO. 33 and SEQ ID NO. 37. An approximately 2.4 kb DNA fragment was recovered by subjecting this PCR product to agarose gel electrophoresis. TatA and TatC expression plasmid pVtatAC was constructed by inserting the recovered DNA fragment into the SmaI site of plasmid pVC7 (Japanese Patent Application Laid-open No. H9-070291). The nucleotide sequence of the constructed plasmid was confirmed using the same method as Example 1. As a result, it was shown that the nucleotide sequence of tatA was slightly different from the predicted sequence of tatA in *C. glutamicum* ATCC13032. The gene sequence encoding this TatA and its 5'-upstream region, as well as the gene sequence encoding TatC are shown in SEQ ID NO. 38.

(3) Construction of TatA, TatB and TatC Expression Plasmid

A region containing the gene sequence encoding TatB predicted in *C. glutamicum* ATCC13032 and the 5'-upstream region thereof, were amplified by PCR using primers having the sequences shown in the following SEQ ID NO. 39 (5'-GAGGCGCTGCCTGAAGATTA-3') and SEQ ID NO. 40 (5'-GACAGGTGAAGAGGTCAAGG-3'). An approximately 1.7 kb DNA fragment was recovered from the amplified PCR product by agarose gel electrophoresis. TatB expression plasmid pVtatB was constructed by inserting the recovered DNA fragment into the SmaI site of plasmid pVC7 (Japanese Patent Application Laid-open No. H9-070291). The nucleotide sequence of the inserted DNA fragment of the constructed plasmid was confirmed using the same method as Example 1. The gene sequence encoding TatB and the gene sequence of the 5' upstream region thereof are described in SEQ ID NO. 41. This TatB expression plasmid pVtatB was digested with restriction enzyme KpnI, and an approximately 1.5 kb DNA fragment was recovered by agarose gel electrophoresis. This DNA fragment contained the tatB promoter region and the gene sequence encoding TatB. Plasmid pVtatABC, which expresses TatA, TatB and TatC, was constructed by inserting this fragment into KpnI site of plasmid pVtatAC produced in (2) of Example 6.

(4) Secretory Expression of Protein-Glutaminase by Strains with an Amplified Tat System Secretion Component

*C. glutamicum* ATCC13869 was transformed with pPKT-PPG produced in (3-2) of Example 3, an expression plasmid for protein-glutaminase having a pro-structure, to produce 13869/pPKT-PPG. Moreover, microbial strains respectively transformed with the above-mentioned plasmids pVtatC, pVtatAC and pVtatABC, and which grew on CM2G agar medium containing 25 mg/l of kanamycin and 5 mg/l of chloramphenicol, were selected to obtain 13869/pPKT-PPG/pVtatC, 13869/pPKT-PPG/pVtatAC and 13869/pPKT-PPG/pVtatABC, respectively. These strains were cultured for 48 hours at 30° C. in MM medium containing 25 mg/l of kanamycin and 5 mg/l of chloramphenicol. Following completion of culturing, as a result of analyzing 10 μl of culture supernatant by SDS-PAGE using the method described in (2-3) of Example 2, 13869/pPKT-PPG/pVtatC, 13869/pPKT-PPG/pVtatAC and 13869/pPKT-PPG/pVtatABC, in which the Tat system secretion component had been amplified, were observed to exhibit considerably a greater amount of secretion in comparison with the strain 13869/pPKT-PPG prior to amplification of the Tat system secretion component. As a result of analyzing each supernatant by reverse phase HPLC under the conditions described in Example 2, the secreted amount was observed to be roughly three times greater in 13869/pPKT-PPG/pVtatC and 13869/pPKT-PPG/pVtatAC than in 13869/pPKT-PPG, and roughly ten times greater in 13869/pPKT-PPG/pVtatABC than in 13869/pPKT-PPG.

EXAMPLE 7

Effect of Amplification of Tat System Secretion Component on Secretion Amount of Transglutaminase Using IMD Signal Derived from *Arthrobacter globiformis*

(1) Generation of Transglutaminase Secretory Expression Plasmid Containing IMD Signal from *Arthrobacter globiformis*

Using the isomaltodextranase secretory expression plasmid pPKI-IMD prepared in Example 1 as a template, a region containing the IMD signal sequence and CspB promoter of the 5' upstream region thereof was amplified with primers having the sequences shown in SEQ ID NO. 14 and SEQ ID NO. 42 (5'-GTCTCTTCCCCCGCGCCATTGTCGGC-CTGGGCGGAGCCTGC-3'). SEQ ID NO. 42 contained a gene sequence encoding the C-terminal side of the IMD signal sequence and a gene sequence encoding the N-terminal side of the pro-sequence of transglutaminase. In addition, using pPKSPTG1 (described in WO 01/23591) as a template, PCR was carried out using primers having the sequences shown in SEQ ID NO. 43 (5'-GACAATGGCGCGGGG-GAAG-3') and SEQ ID NO. 44 (5'-GACAATG-GCGCGGGGG AAG-3') to amplify a gene sequence encoding transglutaminase having pro-structure. The PCR product which had been amplified by the primers having the sequences shown in SEQ ID NO. 14 and SEQ ID NO. 42, and the PCR product which had been amplified by the primers having the sequences shown in SEQ ID NO. 43 and SEQ ID NO. 44 were mixed in a 1:1 ratio and were used as templates, and crossover PCR was carried out using the primers having the sequences shown in SEQ ID NO. 14 and SEQ ID NO. 44 to amplify a fusion gene containing the CspB promoter, the IMD signal and the gene encoding transglutaminase having pro-structure. This PCR product was cleaved with restriction enzymes ScaI and EcoO65I, and an approximately 700 bp gene fragment was recovered through agarose gel electrophoresis. An expression plasmid for transglutaminase with pro-structure, pPKI-PTG1, was produced by inserting the recovered DNA fragment into ScaI-EcoO65I site of pPK-SPTG1 (described in WO01/23591). The nucleotide sequence of the produced plasmid was determined according to the method described in Example 1, and the presence of the predicted fusion gene was confirmed.

(2) Secretory Expression of Transglutaminase Using an IMD Signal in Strains Having an Amplified Tat System Secretion Component Strain 13869/pPKIPTG1 was produced by transforming *C. glutamicum* ATCC13869 with plasmid pPKI-PTG1 produced in (1). After additionally transforming this strain with the expression plasmid expressing Tat secretion component TatA and TatB and TatC, pVtatABC, produced in (3) of Example 6, a microbial strain that grew on CM2G agar medium containing 25 mg/l of kanamycin and 5 mg/l of chloramphenicol was selected to obtain the Tat system secretion component amplified strain 13869/pPKI-PTG1/pVtatABC.

13869/pPKI-PTG1 and 13869/pPKI-PTG1/pVtatABC were cultured for 48 hours at 30° C. in MM medium containing 25 mg/l of kanamycin and 5 mg/l of chloramphenicol. Following completion of culturing, as a result of subjecting the culture supernatant to SDS-PAGE using the method described in (2-3) of Example 2, the secreted amount of transglutaminase having pro-structure was observed to increase in 13869/pPKI-PTG1/pVtatABC as compared with 13869/pPKI-PTG1. Moreover, as a result of assaying the culture supernatant by reverse phase HPLC under the conditions described in Reference Example A-3, the secreted amount was roughly 7 times higher in the Tat system secretion component enhanced strain.

EXAMPLE 8

Effect of Amplification of Tat System Secretion Component on Secretion Amount of Transglutaminase Using the TorA Signal Derived from *E. coli*

(1) Construction of an Expression Plasmid for Transglutaminase Using TorA Signal from *E. coli*

Using as a template an expression plasmid for protein glutaminase containing the TorA signal, pPKT-PG produced according to (3-2) of Example 3, a region containing the TorA signal sequence and the CspB promoter of the 5'-upstream region thereof was amplified by primers having the sequences shown in SEQ ID NO. 14 and SEQ ID NO. 45 (5'-CTTC-CCCCGCGCCATTGTCCGCAGTCGCACGTCGCGGCG-3'). The sequence described in SEQ ID NO. 45 contained a gene encoding the C-terminal of the TorA signal sequence and a gene encoding the N-terminal of the pro-sequence of transglutaminase. In addition, using pPKSPTG1 (WO01/23591) as a template, PCR was carried out using primers having the sequences shown in SEQ ID NO. 43 and SEQ ID NO. 44 to amplify a gene sequence encoding the transglutaminase having pro-structure. The PCR product amplified with the primers having the sequences shown in SEQ ID NO. 14 and SEQ ID NO. 45, and the PCR product amplified with the primers having the sequences shown in SEQ ID NO. 43 and SEQ ID NO. 44 were mixed in a 1:1 ratio and were used as templates, and crossover PCR was carried out with the primers having the sequences shown in SEQ ID NO. 14 and SEQ ID NO. 44 to amplify a fusion gene containing the CspB promoter, the TorA signal and the gene encoding transglutaminase having a pro-structure. This PCR product was cleaved with ScaO and EcoO65I, and an approximately 700 bp gene fragment was recovered through agarose gel electrophoresis. An expression plasmid for transglutaminase with pro-structure, pPKT-PTG1, was produced by inserting this recovered DNA fragment into the ScaI-EcoO65I site of pPK-SPTG1 (WO 01/23591). The nucleotide sequence of the produced plasmid was determined according to the previously described method, and the presence of the predicted fusion gene was confirmed.

(2) Secretory Expression of Transglutaminase Using a TorA Signal in Strains Having an Amplified Tat System Secretion Component Strain 13869/pPKT-PTG1 was produced by transforming *C. glutamicum* ATCC13869 with plasmid pPKT-PTG1 produced in (1) of Example 8. After additionally transforming this strain with Tat secretion component TatA and TatB and TatC expression plasmid pVtatABC produced in Example 8, a microbial strain that grew in CM2G agar medium containing 25 mg/l of kanamycin and 5 mg/l of chloramphenicol was selected to obtain Tat system secretion component enhanced strain 13869/pPKT-PTG1/pVtatABC.

13869/pPKI-PTG1 and 13869/pPKT-PTG1/pVtatABC were cultured for 48 hours at 30° C. in MM medium containing 25 mg/l of kanamycin and 5 mg/l of chloramphenicol. Following completion of culturing, as a result of subjecting 10 μl of culture supernatant to SDS-PAGE using the method described in (2-3) of Example 2, the secreted amount of transglutaminase having pro-structure was observed to increase in 13869/pPKT-PTG1/pVtatABC as compared with 13869/pPKT-PTG1. In addition, as a result of assaying the culture supernatant by reverse phase HPLC under the same conditions as described in Reference Example A-3, the secreted amount was roughly 40 times higher in the Tat system secretion component enhanced strain.

EXAMPLE 9

Alteration of the C-Terminal of Pro-Sequence in the Secretory Production of Protein-Glutaminase Using a TorA Signal Sequence (1) Alteration of the C-terminal of the Pro-sequence of Protein-Glutaminase The N-terminal amino acid sequence of protein-glutaminase for which activity was confirmed in Examples 3 and 5 was analyzed, which revealed that the sequence (NKLASV) had two additional amino acids as compared with naturally-occurring protein-glutaminase. Therefore, the C-terminal sequence of the pro-sequence was altered such that the pro-sequence would be cleaved to produce the N-terminal sequence of naturally occurring protein-glutaminase. Although the C-terminal sequence of the pro-sequence of naturally-occurring protein-glutaminase is "QTNK", it was altered to "FGPK", which is predicted to be easily cleaved by SAM-P45, or to "FGPF", "FAPF", "FAPY", "AHAY", "AHAL", "AAPF", "AAPY" or "AAPM", which are predicted to be easily cleaved with Alkalase (Novozymes) containing subtilisin for its main component. Alteration to "FGPK" was carried out by using primers having the sequences shown in SEQ ID NO. 50 (CTT GGG GCC GAA GCC CTT GAC TTC TTT GGT CAG) and SEQ ID NO. 51 (TTC GGC CCC AAG TTG GCG TCC GTC ATT CCA GAT). The sequence of SEQ ID NO. 50 is a primer for amplifying the pro-sequence region, while the sequence of SEQ ID NO. 51 is a primer for amplifying the mature region. Using plasmid pPKT-PPG constructed in (3-2) of Example 3 as a template, the pro-sequence region of protein-glutaminase was amplified using primers having the sequences shown in SEQ ID NO. 20 and SEQ ID NO. 50, while the mature region of protein-glutaminase was amplified using primers having the sequences shown in SEQ ID NO. 51 and SEQ ID NO. 18. Moreover, these PCR products were mixed in a 1:1 ratio and then using them as templates, crossover PCR was carried out using primers having the sequences shown in SEQ ID NO. 20 and SEQ ID NO. 18 to amplify a protein-glutaminase gene having pro-structure in which the C-terminal pro-sequence had been altered to FGPK.

The crossover PCR product was cloned into SmaI site of pUC18 (pUCPPG (FGPK)) and sequenced to confirm that the pro-sequence had been altered. Then, an AatII-BstPI (large) fragment of pPKT-PPG and an AatII-BstPI (small) fragment of pUCPG (FGPK) were combined together to generate pPKT-PPG (FGPK). Similarly, for alteration to "FGPF" primers having the sequences shown in SEQ ID NO. 52 (GAA GGG GCC GAA GCC CTT GAC TTC TTT GGT CAG) and SEQ ID NO. 53 (TTC GGC CCC TTC TTG GCG TCC GTC ATT CCA GAT) were used, for alteration to "FAPF" primers having the sequences shown in SEQ ID NO. 54 (GAA GGG CGC GAA GCC CTT GAC TTC TTT GGT CAG) and SEQ ID NO. 55 (TTC GCG CCC TTC TTG GCG TCC GTC ATT CCA GAT), for alteration to "FAPY" primers having the sequences shown in SEQ ID NO. 56 (GTA GGG CGC GAA GCC CTT GAC TTC TTT GGT CAG) and SEQ ID NO. 57 (TTC GCG CCC TAC TTG GCG TCC GTC ATT CCA GAT), for alteration to "AHAY" primers having the sequence shown in SEQ ID NO. 58 (GTA CGC GTG CGC GCC CTT GAC TTC TTT GGT CAG) and SEQ ID NO. 59 (GCG CAC GCG TAC TTG GCG TCC GTC ATT CCA GAT), for alteration to "AHAL" primers having the sequences shown in SEQ ID NO. 60 (CAA CGC GTG CGC GCC CTT GAC TTC TTT GGT CAG) and SEQ ID NO. 61 (GCG CAC GCG TTG TTG GCG TCC GTC ATT CCA GAT), for alteration to "AAPF" primers having the sequence shown in SEQ ID NO. 62 (GAA GGG CGC CGC GCC CTT GAC TTC TTT GGT CAG) and SEQ ID NO. 63 (GCG GCG CCC TTC TTG GCG TCC GTC ATT CCA GAT), for alteration to "AAPY" primers having the sequences shown in SEQ ID NO. 64 (GTA GGG CGC CGC GCC CTT GAC TTC TTT GGT CAG) and SEQ ID NO. 65 (GCG GCG CCC TAC TTG GCG TCC GTC ATT CCA GAT) were used, and for alteration to "AAPM" primers having the sequences shown in SEQ ID NO. 66 (CAT GGG CGC CGC GCC CTT GAC TTC TTT GGT CAG) and SEQ ID NO. 67 (GCG GCG CCC ATG TTG GCG TCC GTC ATT CCA GAT) were used. The sequences of SEQ ID NO. 52, 54, 56, 58, 60, 62, 64 and 66 are primers for amplifying the pro-sequence region, while the sequences of SEQ ID NO. 53, 55, 57, 59, 61, 63, 65 and 67 are primers for amplifying the mature region. Using as a template plasmid pPKT-PPG constructed in (3-2) of Example 3, the pro-sequence region of protein-glutaminase was amplified with primers having the sequences shown in SEQ ID NO. 20 and SEQ ID No. 52, while the mature region of protein-glutaminase was amplified using primers having the sequences shown in SEQ ID NO. 53 and SEQ ID NO. 18, respectively. These PCR products were mixed in a 1:1 ratio, and then using them as templates, crossover PCR was carried out using primers having the sequences shown in SEQ ID NO. 20 and SEQ ID NO. 18 to amplify protein-glutaminase gene having a pro-structure in which the C-terminal of the pro-sequence was altered to FGPF. The cross over PCR product was cloned into SmaI site of pUC18 (pUCPG (FGPF)) and sequenced to confirm that the pro-sequence had been altered. Then, an AatII-BstPI (large) fragment of pPKT-PPG and an AatII-BstPI (small) fragment of pUCPPG (FGPF) were combined to generate pPKT-PPG (FGPF). According to the similar procedures, pPKT-PPG (FAPF), pPKT-PPG (FAPY), pPKT-PPG (AHAY), pPKT-PPG (AHAL), pPKT-PPG (AAPF), pPKT-PPG (AAPY) and pPKT-PPG (AAPM) were constructed.

(2) Secretion and Expression of Protein-Glutaminase in Which the C-terminal of the Pro-Sequence has Been Altered to "FGPK"

C. Glutamicum ATCC13869 was transformed with the constructed plasmid pPKT-PPG (FGPK), and a microbial strain which grew in CM2G agar medium containing 25 mg/l of kanamycin was selected. The selected strain was cultured for 48 hours at 30° C. in MM liquid medium containing 25 mg/l of kanamycin. Following completion of culturing, 10 µl of culture supernatant were analyzed by SDS-PAGE. SDS-PAGE was carried out using 4-20% gradient gel (Daiichi Pure Chemicals), followed by protein staining with Coomassie Brilliant Blue. As a result, a band was detected in the vicinity of about 35 kDa, which is close to the predicted molecular weight. As a result of analyzing 100 µl of culture supernatant by reverse phase HPLC, the protein concentration was found to be about 20 mg/l.

Moreover, after treating the culture supernatant with Ultrafree (Millipore) as described in (2-2) of Example 2, the protein was enzymatically digested with Actinomycetes-derived protease SAM-P45 to cleave the pro-structure region of protein-glutaminase and to obtain the mature protein. The activity of this mature protein was measured using the method described in Japanese Patent Application Laid-open No. 2000-50887, and the secreted protein was confirmed to actually have protein-glutaminase activity. In addition, as a result of analyzing the N-terminal amino acid sequence of the mature protein, the N-terminal was confirmed to be LASV which was identical to the naturally occurring form. Moreover, it was also confirmed that an N-terminal identical to the naturally occurring form was also obtained when trypsin or Protease M (Amano Enzyme) was used for the maturation.

(3) Secretory Expression of Protein-Glutaminase Having Altered Pro-Sequence C□ Terminal and Maturation thereof by Alkalase C. glutamicum ATCC13869 was respectively transformed with the constructed plasmids pPKT-PPG(FGPF), pPKT-PPG(FAPF), pPKT-PPG(FAPY), pPKT-PPG(AHAY), pPKT-PPG(AHAL), pPKT-PPG(AAPF), pPKT-PG(AAPY) and pPKT-PPG(AAPM), and microbial strains were selected which grew on CM2G agar medium containing 25 mg/l of kanamycin. Each selected strain was cultured for 48 hours at 30° C. in MM liquid medium containing 25 mg/l of kanamycin. Following completion of culturing, 10 µl of culture supernatant were analyzed by SDS-PAGE. SDS-PAGE was carried out using 4-20% gradient gel (Daiichi Pure Chemicals), followed by protein staining with Coomassie Brilliant Blue. As a result, a band was detected in the vicinity of about 35 kDa, which is close to the predicted molecular weight. As a result of analyzing 100 µl of culture supernatant by reverse phase HPLC, the protein concentration was found to be about 20 mg/l.

Moreover, after treating the culture supernatant with Ultrafree (Millipore) in the same manner as (2-2) of Example 2, the protein was enzymatically digested subtilisin (Sigma) or Alkalase (Novozymes) to cleave the pro-structure region of protein-glutaminase and to obtain the mature protein. The activity of this mature protein was measured using the method described in Japanese Patent Application Laid-open No. 2000-50887, and the secreted protein was confirmed to have protein-glutaminase activity. In addition, as a result of analyzing the N-terminal amino acid sequence of the mature protein, it was confirmed that the N-terminal was LASV which was identical to the naturally occurring form.

According to the present invention, an industrially useful heterologous protein for which secretion was difficult through the Sec system which is a protein secretion pathway in Coryneform bacteria, such as isomaltodextranase or protein-glutaminase, can be efficiently produced and secreted (secreted and produced) extracellularly. Namely, according to the present invention, a method is provided for efficiently producing a heterologous protein for which secretory production was difficult through the Sec system.

REFERENCES

1. U.S. Pat. No. 4,965,197
2. Japanese International Patent Application Laid-open No. 6-502548
3. Japanese Patent Application Laid-open No. H11-169182
4. International Publication WO 02/81694
5. Japanese Patent Application Laid-open No. H6-169780
6. Japanese Patent Application Laid-open No. H6-277073
7. Japanese Patent Application Laid-open No. H11-169182
8. Japanese Patent Application Laid-open No. H7-107981
9. U.S. Pat. No. 6,022,952
10. U.S. Pat. No. 6,335,178
11. International Publication WO 02/22667
12. Liebl W, Sinskey A J, Schleifer K H, Expression, secretion, and processing of staphylococcal nuclease by *Corynebacterium glutamicum*, J. Bacteriology (1992), 174, 1854-1861
13. Billman-Jacobe H, Wang L, Kortt A, Stewart D, Radford A, Expression and secretion of heterologous proteases by *Corynebacterium glutamicum*, Applied Environmental Microbiology, (1995), 61, 1610-1613
14. Salim K, Haedens V, Content J, Leblon G, Huygen K, Heterologous expression of the *Mycobacterium tuberculosis* gene encoding antigen 85A in *Corynebacterium glutamicum*, Applied Environmental Microbiology, (1997), 63, 4392-4400
15. Kikuchi Y, Date M, Yokoyama K, Umezawa Y, Matsui H, Secretion of active-form *Streptoverticillium mobaraense* transglutaminase by *Corynebacterium glutamicum*: processing of the pro-transglutaminase by a cosecreted subtilisin-like protease from *Streptomyces albogriseolus*, Applied Environmental Microbiology, (2003), 69, 358-366
16. Chaddock A M, Mant A, Karnauchov I, Brink S, Herrmann R G, Klosgen R B, Robinson C, A new type of signal peptide: central role of a twin-arginine motif in transfer signals for the delta pH-dependent thylakoidal protein translocase, EMBO Journal, (1995), 14, 2715-2722

17. Mark Settles, Ann Yonetani, Aimee Baron, Daniel R. Bush, Kenneth Cline and Rob Martienssen, Sec-Independent Protein Translocation by the Maize Hcf106 Protein, Science, (1997), 278, 1467-1470

18. Jongbloed J D, Martin U, Antelmann H, Hecker M, Tjalsma H, Venema G, Bron S, van Dijl J M, Muller J, TatC is a specificity determinant for protein secretion via the twin-arginine translocation pathway, Journal of Biological Chemistry, 275, 41350-41357

19. Hynds P J, Robinson D, Robinson C, The sec-independent twin-arginine translocation system can transport both tightly folded and malfolded proteins across the thylakoid membrane. J. Biol Chem. (1998) 25;273(52): 34868-74

20. Barrett, C. M., N. Ray, J. D. Thomas, C. Robinson, and A. Bolhius, Quantitative export of a reporter protein, GFP, by the twin-arginine translocation pathway in *Escherichia coli*. (2003) Biochem. Biophys. Res. Commun. 304: 279-284

<Sequence Listing Free Text>

SEQ ID NO. 11-27, 33, 34, 36, 37, 39, 40, 42-45, and 50-67: Synthetic oligonucleotides

The invention claimed is:

1. A method of producing a heterologous protein, comprising
   A) culturing a coryneform bacterium harboring an expression construct comprising a promoter which functions in coryneform bacteria, a nucleic acid sequence which encodes a Tat system-dependent signal peptide, and a nucleic acid sequence which encodes the heterologous protein in the direction from 5'-end to 3'-end, wherein one or more genes encoding a tat system secretion component is amplified in said cornyform bacterium, and
   B) producing and secreting the heterologous protein.

2. The method according to claim 1, wherein the signal peptide is the signal peptide of trimethylamine-N-oxide reductase.

3. The method according to claim 2, wherein the signal peptide comprises the sequence shown in SEQ ID NO. 8.

4. The method of claim 1, wherein the heterologous protein is glutaminase.

5. The method of claim 1, wherein the heterologous protein is isomaltodextranase.

6. The method of claim 1, wherein the gene encoding the tat system secretion component is from a coryneform bacterium.

7. The method according to claim 1, wherein the gene encoding the tat system secretion component is from C. glutamicum.

8. The method according to claim 7, wherein the gene encoding the tat system secretion component is selected from the group consisting of tatA, tatB, tatC, and tatE.

9. The method according to claim 8, wherein tatA encodes a protein comprising the amino acid sequence of SEQ ID NO: 46, tatB encodes a protein comprising the amino acid sequence of SEQ ID NO:47, tatC encodes a protein comprising the amino acid sequence of SEQ ID NO: 10 and tatE encodes a protein comprising the amino acid sequence of SEQ ID NO: 49.

10. The method according to claim 1, wherein the signal peptide is the signal peptide of isomaltodextranase.

11. The method according to claim 10, wherein the signal peptide comprises the sequence shown in SEQ ID NO. 6.

12. The method according to claim 1, wherein the signal peptide comprises the sequence selected from the group consisting of SEQ ID NO. 31, SEQ ID NO. 32, SEQ ID NO. 28, SEQ ID NO. 29, and SEQ ID NO. 30.

* * * * *